United States Patent
Thayumanavan et al.

(10) Patent No.: US 12,214,086 B2
(45) Date of Patent: Feb. 4, 2025

(54) SURFACE FUNCTIONALIZED, HOST-GUEST POLYMER NANO-ASSEMBLIES AND METHODS THEREOF

(71) Applicant: University of Massachusetts, Boston, MA (US)

(72) Inventors: Sankaran Thayumanavan, Amherst, MA (US); Jiaming Zhuang, Amherst, MA (US); Hui Wang, Sunderland, MA (US)

(73) Assignee: University of Massachusetts, Boston, MA (US)

( * ) Notice: Subject to any disclaimer, the term of this patent is extended or adjusted under 35 U.S.C. 154(b) by 449 days.

(21) Appl. No.: 17/390,912

(22) Filed: Jul. 31, 2021

(65) Prior Publication Data

US 2022/0133639 A1 May 5, 2022

Related U.S. Application Data

(63) Continuation of application No. 15/025,060, filed as application No. PCT/US2014/058751 on Oct. 2, 2014, now abandoned.

(60) Provisional application No. 61/886,016, filed on Oct. 2, 2013.

(51) Int. Cl.
*A61K 9/51* (2006.01)
*A61K 47/69* (2017.01)

(52) U.S. Cl.
CPC ........ *A61K 9/5138* (2013.01); *A61K 47/6903* (2017.08); *A61K 9/5146* (2013.01); *Y10S 977/773* (2013.01); *Y10S 977/906* (2013.01)

(58) Field of Classification Search
None
See application file for complete search history.

(56) References Cited

U.S. PATENT DOCUMENTS

| | | | |
|---|---|---|---|
| 9,592,302 B2* | 3/2017 | Thayumanavan | .. C08F 220/385 |
| 10,358,531 B2* | 7/2019 | Thayumanavan | .... C08F 226/02 |
| 2014/0370114 A1* | 12/2014 | Lee | ........................ C08F 120/06 |
| | | | 526/341 |

OTHER PUBLICATIONS

Shivshankar R. Mane et al. "Amphiphilic Homopolymer Vesicles as Unique Nano-Carriers for Cancer Therapy." Macromolecules, vol. 45, 2012, pp. 8037-8042 and 9 pages of supplemental information. (Year: 2012).*

Merriam-Webster Dictionary. "Homopolymer Definition & Meaning." https://www.merriam-webster.com/dictionary/homopolymer accessed Dec. 26, 2023, 5 printed pages. (Year: 2023).*

Shivshankar R. Mane et al. "Amphiphilic Homopolymer Vesicles as Unique Nano-Carriers for Cancer Therapy." Macromolecules, vol. 45, 2012, pp. 8037-8042 and 9 pages of supporting information. (Year: 2012).*

(Continued)

*Primary Examiner* — Isaac Shomer
(74) *Attorney, Agent, or Firm* — Milstein Zhang & Wu LLC

(57) ABSTRACT

The invention generally relates to polymer-based nanostructures. More particularly, the invention relates to novel, surface-functionalized, guest-host polymer nano-assemblies and nano-delivery vehicles useful in diverse fields including drug delivery, diagnostics and specialty materials. The nano-assemblies and nano-delivery vehicles of the invention are afforded via simplify and reliable approaches.

14 Claims, 23 Drawing Sheets

(56) References Cited

OTHER PUBLICATIONS

Reuben T. Chacko et al. "Polymer nanogels: A versatile nanoscopic drug delivery platform." Advanced Drug Delivery Reviews, vol. 64, 2012, pp. 863-851. (Year: 2012).*

Subhadeep Basu et al. "Invertible Amphiphilic Homopolymers." Journal of the American Chemical Society Communications, vol. 126, 2004, pp. 9890-9891. (Year: 2004).*

* cited by examiner

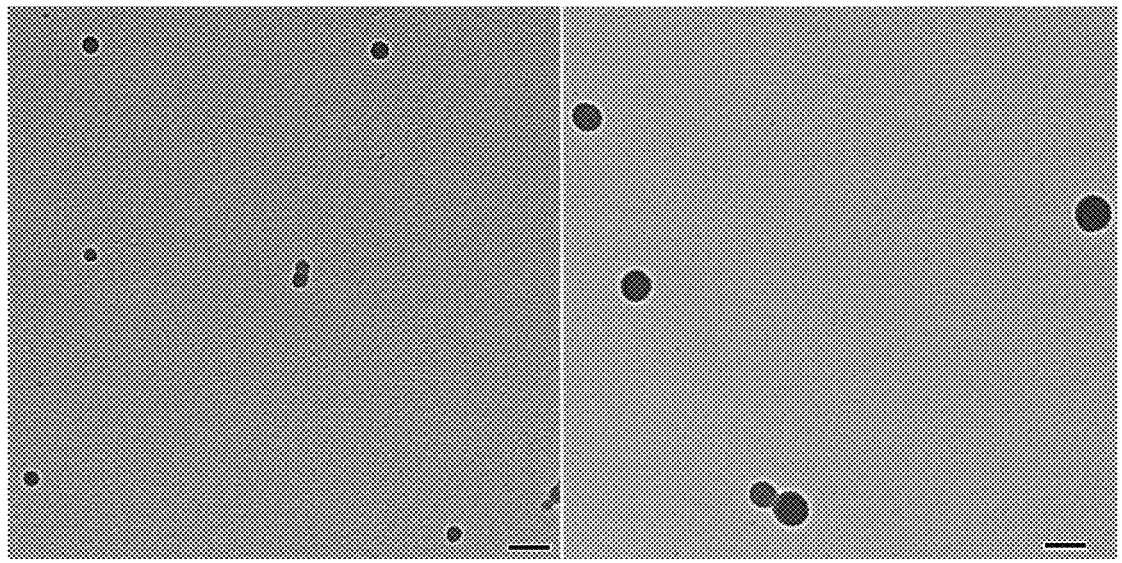
FIG. 28
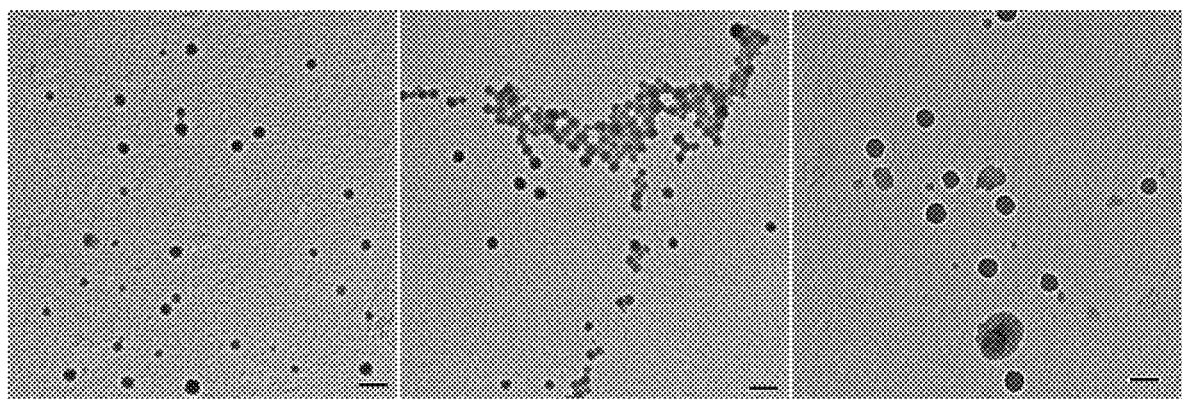

SURFACE FUNCTIONALIZED, HOST-GUEST POLYMER NANO-ASSEMBLIES AND METHODS THEREOF

PRIORITY CLAIMS AND RELATED APPLICATIONS

This application is a continuation of U.S. Ser. No. 15/025,060, filed Mar. 25, 2016, which is the U.S. national phase of and claims priority to PCT/US14/58751, filed Oct. 2, 2014, which claims the benefit of priority from U.S. Provisional Application Ser. No. 61/886,016, filed Oct. 2, 2013, the entire content of each of which is incorporated herein by reference in its entirety.

GOVERNMENT RIGHTS

The United States Government has certain rights to the invention pursuant to Grant No. CHE-1307118 from National Science Foundation (NSF), and Grant No. 5RO1GM065255 from National Institutes of Health (NIH), Grant No. W911NF1010313 from U. S. Army Research Office, Grant No. CMMI-1025020 from NSF-NSEC and Grant No. DMR-0820506 from NSF-MRSEC.

TECHNICAL FIELDS OF THE INVENTION

The invention generally relates to polymer-based nanostructures. More particularly, the invention relates to novel, surface-functionalized, guest-host polymer nano-assemblies and nano-delivery vehicles useful in diverse fields including drug delivery, diagnostics and specialty materials.

BACKGROUND OF THE INVENTION

Nanoparticles have had a significant impact on a variety of areas such as microelectronics, multiphase catalysis, sensing and therapeutics. (*Nanoparticles: From Theory to Application*; Schmid, Ed.; Wiley-VCH: Essen, 2004; Zhang, et al. *Self-Assembled Nanostructures*; Nanostructure Science and Technology Series; Springer: 2002; *Nanoparticles: Building Blocks for Nanotechnology*; Rotello, Ed.; Springer: 2003; Daniel, et al. 2004 *Chem. Rev.* 104, 293.) For most applications, facile modulation of the nanoparticle surface is critical in order to obtain appropriate interfacial properties. The ability to encapsulate and release guest molecules within the nanoparticle interior is also required for applications such as sensing and therapeutics.

A platform that affords both surface functionalization and guest encapsulation in a single nanoscopic scaffold is highly desirable. Nanoscale materials, such as metallic or semiconductor nanoparticles and dendrimers, are excellent scaffolds for displaying surface functional groups. (Giljohann, et al. 2010 *Angew. Chem. Int. Ed.* 49, 3280-3294; Saha, et al. 2012 *Chem. Rev.* 112, 2739-2779; Khandare, et al. 2012 *Chem. Soc. Rev.* 41, 2824-2848; Grayson, et al. 2001 *Chem. Rev.* 101, 3819-3867; Arima, et al. 2012 *Pharmaceutics* 4, 130-148.) For example, monolayer protection of gold nanoparticles is easily achieved with thiol-bearing molecules due to the high affinity of thiol moiety toward gold nanoparticles. However, these scaffolds generally lack features that allow for favorable non-covalent host-guest interactions. In contrast, amphiphilic molecules readily self-assemble into nanoassemblies, such as micelles and liposomes, which can encapsulate guest molecules within their interior spaces. (Harada, et al. 2006 *Progress in Poly. Sci.* 31, 949-982; O'Reilly, et al. 2006 *Chem. Soc. Rev.* 35, 1068-1083; Zhu, et al. 2012 *J. Mat. Chem.* 22, 7667-7671; Owen, et al. 2012 *Nano Today* 7, 53-65; Sawant, et al. 2010 *Soft Matter* 6, 4026-4044; Micheli, et al. 2012 *Recent Patents on CNS Drug Discovery* 7, 71-86.)

Nevertheless, modifying their surface functional groups are challenging because these modifications often result in changes in the hydrophilic-lipophilic balance that is necessary for retention of the fidelity of the assembly. Surface functionalizable polymeric nanoparticles often require rigorous processing conditions. Additionally, size variations are limited and difficult to achieve and control.

Polymer vesicles, or polymersomes have been generated and extensively investigated as drug delivery vehicles, diagnostics, nanoreactors and artificial organelles. (Tanner, et al. 2011 *Acc. Chem. Res.* 44, 1039-1049; Vriezema, et al. 2007 *Angew. Chem. Int. Ed.* 46, 7378-7382; Wang, et al. 2012 *Angew. Chem. Int. Ed.* 51, 11122-11125; Lomas, et al. 2007 *Adv. Mater.* 19, 4238-4243; Choucair, et al. 2005 *Langmuir* 21, 9308-9313; Ben-Haim, et al. 2008 *Nano Lett.* 8, 1368-1373; Ghoroghchian, et al. 2005 *PNAS* 102, 2922-2927; Choi, et al. 2005 *Nano Lett.* 5, 2538-2542; Sanson, et al. 2011 *ACS Nano* 5, 1122-1140; Ahmed, et al. 2006 *J. Control. Releas.* 116, 150-158.)

The potential advantages of polymeric vesicle compared with their lipid counterparts arise from the enhanced colloidal stability, tunable membrane thickness and permeability, and engineered surface functionalities. However, a remaining challenge involves the unstable nature of the non-covalently organized supramolecular assembly of the polymersome, which causes morphological changes. The morphological changes can be due to the change in solvent composition during the dialysis to remove organic solvent in polymersome formation process or due to the post-functionalization that changes hydrophilic lipophilic balance (HLB) of the precursor polymer resulting in loss of fidelity of the assembly. (Du, et al. 2009 *Soft Matter* 5, 3544-3561; Su, et al. 2014 *ACS Macro Lett.* 3, 534-539.)

Additionally, like other self-assembled systems polymersomes also undergo disassembly upon dilution, solvent exposure and interaction with their surroundings depending on the specific applications. (Savariar, et al. 2008 *J. Am. Chem. Soc.* 130, 5416-5417.) To address these issues, the formation of vesicle by solvation of polymer in aqueous media followed by the chemical crosslinking can be a good solution. Unfortunately, chemistries developed for polymersome post-functionalization, direct dissolution method and efficient cross-linking chemistry for aqueous solution are all quite limited. (Egli, et al. 2011 *J. Am. Chem. Soc.* 133, 4476-4483; Opsteen, et al. 2007 *Chem. Commun.* 30, 3136-3138; Li, et al. 2007 *Chem. Commu.* 30, 5217-5219; Rosselgong, et al. 2012 *ACS Macro Lett.* 1, 1041-1045.)

Another challenge for polymersome preparation is to control the size that is critical for their applications. (Harashima, et al. 1996 *Adv. Drug Delivery Rev.* 19, 425-444.) Although polymersomes with tunable size can be achieved by varying the block length, concentration of copolymers and ratio of solvents, the preparation of vesicle-forming copolymers with complex architectures like block, graft or dendritic copolymer requires demanding synthetic effort even with the aid of the robust polymerization techniques. (Xu, et al. 2009 *J. Mater. Chem.* 19, 4183-4190; Anraku, et al. 2010 *J. Am. Chem. Soc.* 132, 1631-1636; Blanazs, et al. 2012 *Macromolecules* 45, 5099-5107; Zhou, et al. 2004 *Angew. Chem. Int. Ed.* 43, 4896-4899; Azzam, et al. 2006 *Angew. Chem. Int. Ed,* 45, 7443-7447; Sun, et al. 2009 *ACS Nano* 3, 673-681; Wang, et al. 2001 *J. Colloid. Interf. Sci.* 237, 200-207.)

Capability of facile formation of polymersome from easily accessible polymers with simple architectures will open a new avenue to prepare customized polymersomes. Directed by the potential applications, the "intelligent" polymersomes that are capable of adapting to the environmental changing are really desired. (Bellomo, et al. 2004 *Nat. Mater.* 3, 244-248; Napoli, et al. 2004 *Nat. Mater.* 3. 183-189; Yan, et al. 2013 *Angew. Chem. Int. Ed.* 52, 5070-5073; Liu, et al. 2014 *J. Am. Chem. Soc.* 136, 7492-7497; Liu, et al. 2006 *Angew. Chem. Int. Ed.* 45, 3846-3850.)

Thus, there is an urgent need for simplified and reliable approaches to functionalizable polymer nanoparticles and delivery vehicles. Additionally, challenges remain for "intelligent" polymersomes and simple methods to their preparation.

SUMMARY OF THE INVENTION

The invention relates to novel, surface-functionalized/functionalizable, guest-host polymer nano-assemblies and nano-delivery vehicles useful in diverse fields including drug delivery, diagnostics and specialty materials. The functionalized/functionalizable polymer nanoparticles exhibit the advantages of surface functionalization capabilities available in dendrimers and metallic nanoparticles as well as the host-guest features presented in micelles and vesicles. Importantly, the nano-assemblies and nano-delivery vehicles of the invention are afforded via simple and reliable approaches.

The invention also relates to novel novel polymer-based cross-linked nanoparticle with vesicular structures, or Vesi-Gel, and methods of their preparation. Herein disclosed is an easy and generally applicable method in which a simple and easily obtained amphiphilic homopolymer electrolyte self-assembles into vesicular structure assisted by a variety of multivalent salts based on a salt-bridging mechanism. The VesiGel disclosed herein have been demonstrated to capture the features including: i) organic solvent free formation; ii) tunable nanoscaled sizes; ii) variable surface functionalities; iii) functionalizable corona and membrane; iv) reversible crosslinking stabilization; v) capable of encapsulating hydrophobic and hydrophilic small molecules as well as proteins; v) stimuli-responsive controlled release of encapsulants.

In one aspect, the invention generally relates to a nano-assembly. The nano-assembly includes: (1) a host crosslinked polymer network having a functionalized surface with one or more functional groups; and (2) a guest molecular cargo non-covalently encapsulated in the host crosslinked polymer network. The host crosslinked polymer network is addressable by a biological, physical or chemical intervention resulting in partial or complete decrosslinking of the host polymer network and release of the guest molecular cargo from the nano-assembly.

In another aspect, the invention generally relates to a composition comprising the nano-assembly disclosed herein.

In yet another aspect, the invention generally relates to a method for controlled delivery of an agent to a target biological site. The method includes: (1) providing a nano-assembly of a host crosslinked polymer network non-covalently encapsulating therein a guest molecular cargo, wherein the host crosslinked polymer network is capable of partial or complete decrosslinking by a biological, physical or chemical intervention resulting in release of the guest molecular cargo from the nano-assembly; (2) delivering the nano-assembly to the target biological site; and (3) causing a biological, physical or chemical intervention resulting in a partial or complete decrosslinking resulting in release of the guest molecular cargo from the nano-assembly.

In yet another aspect, the invention generally relates to a nanoparticle. The nanoparticle includes: (1) a shell of a crosslinked polymer network having a surface functionalized with one or more functional groups; and (2) a core comprising a host polymer network and a guest agent non-covalently encapsulated therein. The core and shell of crosslinked polymer network are independently addressable by a biological, physical or chemical intervention resulting in partial or complete disassembly of the shell and/or the core thereby releasing of the guest agent.

In yet another aspect, the invention generally relates to a polymer-based nanoparticle having vesicular structures stabilized by intraparticular crosslinking, wherein the polymer is an amphiphilic homopolymer comprising a hydrophilic head group and a hydrophobic tail group.

In certain embodiments, the hydrophilic head group is selected from charged functional groups such as amino, ammonium, sulfonium, phosphonium, carboxylate, phosphate, phosphonate, sulfate, and sulfonate, groups and charge-neutral functional groups such as carboxy betaine, sulfo betaine, phosphoryl choline, phosphonyl choline, saccharides, and polyethylene glycol groups and the hydrophobic tail group is selected from linear and branched alkyl chains, linear and branched fluoro-substituted alkyl chains, and alkyl chains containing aromatic or heteromatic functional groups.

In yet another aspect, the invention generally relates to a nano-assembly. The nano-assembly includes: a host crosslinked polymer-based nanoparticle disclosed herein; and a guest molecular cargo non-covalently encapsulated in the host crosslinked polymer-based nanoparticle. The host crosslinked polymer network is addressable by a biological or chemical intervention resulting in partial or complete decrosslinking of the host polymer network and release of the guest molecular cargo from the nano-assembly.

In yet another aspect, the invention generally relates to a method for forming a polymer-based nanoparticle disclosed herein. The method includes: providing an amphiphilic homopolymer by a ring opening reaction; causing self-assembly of the amphiphilic homopolymer, induced or assisted by one or more salt, to form a polymersome comprising vesicle structures; and performing an intraparticular crosslinking on the polymersome resulting in intra- and inter-molecularly crosslinked polymer-based nanoparticle having vesicle structures.

In yet another aspect, the invention generally relates to a method for controlled delivery of a molecular cargo to a target biological site. The method includes: providing a nano-assembly disclosed herein; delivering the nano-assembly to the target biological site; and causing a biological or chemical intervention resulting in a partial or complete decrosslinking resulting in release of the guest molecular cargo from the nano-assembly.

BRIEF DESCRIPTION OF THE DRAWINGS

FIG. 28. TEM image of cationic VesiGel prepared in 2.0 mM (left) and 2.5 mM (right) $Na_2SO_3$ solution. The sacle bar is 100 nm.

DEFINITIONS

Figure 1:
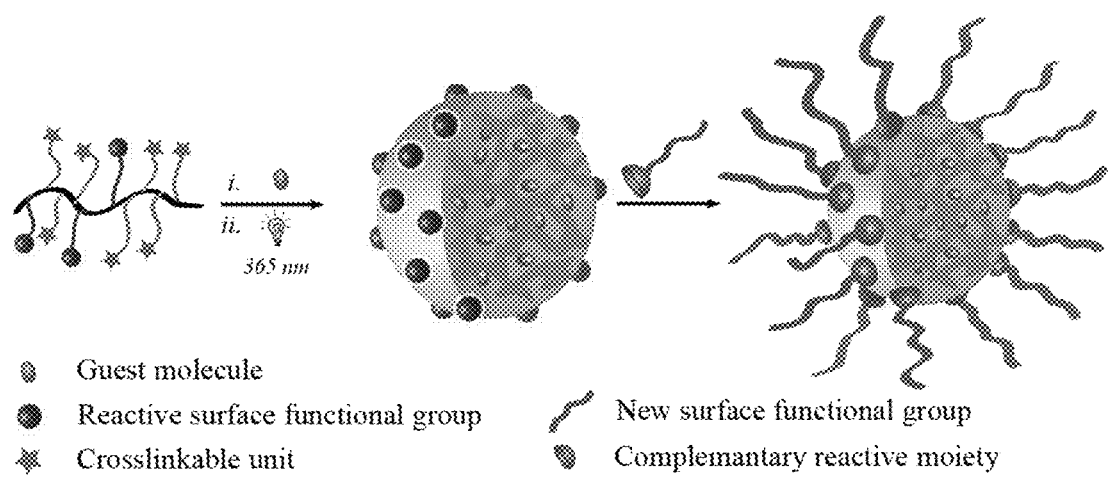
FIG. 1. Schematic representation of the polymer nanoparticle with surface functionalization and guest binding abilities.

Definitions of specific functional groups and chemical terms are described in more detail below. General principles of organic chemistry, as well as specific functional moieties and reactivity, are described in "Organic Chemistry", Thomas Sorrell, University Science Books, Sausalito: 2006. It will be appreciated that the compounds, as described herein, may be substituted with any number of substituents or functional moieties.

As used herein, "$C_x$-$C_y$" refers in general to groups that have from x to y (inclusive) carbon atoms. Therefore, for example, $C_1$-$C_6$ refers to groups that have 1, 2, 3, 4, 5, or 6 carbon atoms, which encompass $C_1$-$C_2$, $C_1$-$C_3$, $C_1$-$C_4$, $C_1$-$C_5$, $C_2$-$C_3$, $C_2$-$C_4$, $C_2$-$C_5$, $C_2$-$C_6$, and all like combinations. "$C_1$-$C_{20}$" and the likes similarly encompass the various combinations between 1 and 20 (inclusive) carbon atoms, such as $C_1$-$C_6$, $C_1$-$C_{12}$ and $C_3$-$C_{12}$.

As used herein, the term "alkyl", refers to a hydrocarbyl group, which is a saturated hydrocarbon radical having the number of carbon atoms designated and includes straight, branched chain, cyclic and polycyclic groups. The term "hydrocarbyl" refers to any moiety comprising only hydrogen and carbon atoms. Hydrocarbyl groups include saturated (e.g., alkyl groups), unsaturated groups (e.g., alkenes and alkynes), aromatic groups (e.g., phenyl and naphthyl) and mixtures thereof.

As used herein, the term "$C_x$-$C_y$" alkyl refers to a saturated linear or branched free radical consisting essentially of x to y carbon atoms, wherein x is an integer from 1 to about 10 and y is an integer from about 2 to about 20. Exemplary $C_x$-$C_y$ alkyl groups include "$C_1$-$C_{20}$ alkyl," which refers to a saturated linear or branched free radical consisting essentially of 1 to 20 carbon atoms and a corresponding number of hydrogen atoms. Exemplary $C_1$-$C_{20}$ alkyl groups include methyl, ethyl, n-propyl, isopropyl, n-butyl, isobutyl, dodecanyl, etc.

As used herein, the term "halogen" refers to fluorine (F), chlorine (Cl), bromine (Br), or iodine (I).

As used herein, the term "biological, physical or chemical interventions" includes a change in pH, redox reagent, redox potential, ionic strength, enzymatic activity, protein concentration, light (e.g., UVA, UVB or UVC), heat, or mechanical stress.

As used herein, "VesiGels" refers to polymer-based crosslinked nanoparticle with vesicular structures disclosed herein.

DETAILED DESCRIPTION OF THE INVENTION

The invention provides surface-functionalized/functionalizable, guest-host polymer nano-assemblies and nano-delivery vehicles useful in diverse fields including drug delivery, diagnostics and specialty materials.

The nano-assemblies and nano-delivery vehicles of the invention can be prepared via simple and reliable synthetic techniques. The nanoparticles of the invention capture the advantages of surface functionalization capabilities available in dendrimers and metallic nanoparticles as well as the host-guest features presented in micelles and vesicles.

In one aspect, the invention generally relates to a nano-assembly. The nano-assembly includes: (1) a host crosslinked polymer network having a functionalized surface with one or more functional groups; and (2) a guest molecular cargo non-covalently encapsulated in the host crosslinked polymer network. The host crosslinked polymer network is addressable by a biological, physical or chemical intervention resulting in partial or complete decrosslinking of the host polymer network and release of the guest molecular cargo from the nano-assembly.

In certain embodiments, the host crosslinked polymer network is a nanogel.

In certain embodiments, the host crosslinked polymer network is formed from a random copolymer via a controlled crosslinking.

In certain embodiments, the polymer network is formed from a homopolymer via a controlled crosslinking.

Depending on the nature of the polymer network and crosslinking, the biological or chemical intervention may be a change in pH, redox reagent, redox potential, ionic strength, enzymatic activity, protein concentration, light, heat, or mechanical stress, which intervention leads to a breaking and/or forming of a chemical bond.

The nano-assembly may take any suitable dimensions, for example, having a diameter from about 3 nm to about 300 nm (e.g., about 3 nm to about 200 nm, about 3 nm to about 100 nm, about 3 nm to about 50 nm, about 3 nm to about 30 nm, about 10 nm to about 300 nm, about 30 nm to about 300 nm, about 50 nm to about 300 nm, about 100 nm to about 300 nm).

The non-covalently encapsulated guest molecular cargo may be present in any suitable amounts, for example, accounting for from about 1 wt % to about 45 wt % (e.g., about 1 wt % to about 35 wt %, about 1 wt % to about 25 wt %, about 1 wt % to about 20 wt %, about 1 wt % to about 15 wt %, about 1 wt % to about 10 wt %, about 5 wt % to about 45 wt %, about 10 wt % to about 45 wt %, about 15 wt % to about 45 wt %, about 20 wt % to about 45 wt %) of the nano-assembly.

The guest molecular cargo may be any suitable material, for example, selected from therapeutic, diagnostic or imaging agents. For example, the guest molecular cargo is a small molecule, a peptide or an oligonucleotide. In certain embodiments, the guest molecular cargo is an antitumor agent.

In certain preferred embodiments, the guest molecular cargo is a hydrophobic molecule.

The functionalized surface of the non-covalently may display one or more reactive groups at any suitable density, for example, from very sparingly (e.g., about 0.1%) to full coverage (e.g., about 100%). Thus, for example, the functionalized surface of the non-covalently may display reactive groups at a density of 1, 2, 5, 10, 20, 30, 40, 50, 60, 70, 80, 90, 100%.

In another aspect, the invention generally relates to a composition comprising the nano-assembly disclosed herein.

In yet another aspect, the invention generally relates to a method for controlled delivery of an agent to a target biological site. The method includes: (1) providing a nano-assembly of a host crosslinked polymer network non-covalently encapsulating therein a guest molecular cargo, wherein the host crosslinked polymer network is capable of partial or complete decrosslinking by a biological, physical or chemical intervention resulting in release of the guest molecular cargo from the nano-assembly; (2) delivering the nano-assembly to the target biological site; and (3) causing a biological, physical or chemical intervention resulting in a partial or complete decrosslinking resulting in release of the guest molecular cargo from the nano-assembly.

Depending on the nature of the polymer network and crosslinking, the biological, physical or chemical intervention is a change in pH, redox reagent, redox potential, ionic strength, enzymatic activity, protein concentration, light, heat, or mechanical stress.

In certain preferred embodiments, the guest molecular cargo is selected from a therapeutic, diagnostic or imaging agent. For example, the guest molecular cargo is a small molecule, a peptide or an oligonucleotide. In certain embodiments, the guest molecular cargo is an antitumor agent.

In certain embodiments, the target biological site comprises a site inside a cell (e.g., a tumor cell).

In certain embodiments, the target biological site comprises a site extracellular to a tumor cell. In certain embodiments, the nano-assembly is preferably taken up by a tumor tissue in a physiological environment.

In yet another aspect, the invention generally relates to a nanoparticle. The nanoparticle includes: (1) a shell of a crosslinked polymer network having a surface functionalized with one or more functional groups; and (2) a core comprising a host polymer network and a guest agent non-covalently encapsulated therein. The shell of crosslinked polymer network is addressable by a biological, physical or chemical intervention resulting in partial or complete dissociation of the shell thereby releasing of the guest agent.

In certain embodiments, the host crosslinked polymer network is formed from a random copolymer via a controlled crosslinking.

In certain embodiments, the host crosslinked polymer network is formed from a homopolymer via a controlled crosslinking.

In certain embodiments, the one or more functional groups are selected from the group consisting of amines, carboxylates, hydroxyl, halides, acyl halides, esters, azides, nitriles, amides, epoxides, aldehydes, furans, alkenes and alkynes.

In certain embodiments, the biological, physical or chemical intervention is a change in pH, redox potential, ionic strength, enzymatic activity, protein concentration, light, heat, or mechanical stress.

For example, certain copolymer-based nanoparticles can be rapidly formed by ultraviolet or visible irradiation without the need to use any chemical crosslinkers or agents. The encapsulated guest molecules can be released by ultraviolet or visible irradiation or in the presence of a chemical stimulus such as glutathione if disulfide-bond-forming moieties (or sulfhydryl groups) are also incorporated into the copolymer structure.

In certain preferred embodiments, the guest molecular cargo is selected from a therapeutic, diagnostic or imaging agent. For example, the guest molecular cargo is a small molecule, a peptide or an oligonucleotide. In certain embodiments, the guest molecular cargo is an antitumor agent.

I. Surface-Functionalized Polymer Nanoparticle Formed from Amphiphilic Copolymers Unique features of the functionalizable copolymer-based nanoparticles include: (i) the precursor polymer is based on a random copolymer; (ii) the polymer self-assembles in a solvent, which can then be converted to nanoparticle in one step without the need for any additional processing; (iii) the nanoparticle contains a surface functional group, which can be further manipulated easily; (iv) the size of the nanoparticle is tunable; and (iv) the interior of the nanoparticle is capable of sequestering guest molecules.

In certain embodiments, the host crosslinked polymer network is formed from a random copolymer via a controlled crosslinking.

In certain preferred embodiments, the random copolymer has the formula of

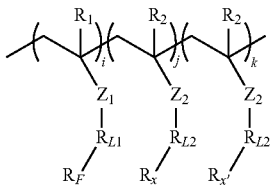

wherein
each of $Z_1$ and $Z_2$ is independently

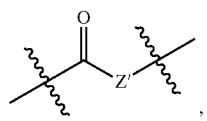

wherein Z' is selected from O, NH, NR (R=$C_1$-$C_6$ alkyl group or $R_F$);
each of $R_1$ and $R_2$ is independently selected from a hydrogen, $C_1$-$C_{12}$ alkyl group, or halogen;
each of $R_{L1}$ and $R_{L2}$ is independently a single bond or a spacer group;
$R_F$ is —H or a functional group;

$R_x$ is a crosslinking group capable of inter- or intra-molecular crosslinking;
$R_{x'}$ is an inter- or intra-molecularly crosslinked group; and
i=a·n, j=x·n, and k=b·n−x·n, wherein each of a and b is a positive number with a+b=1, each of n and x is independently an integer from about 0.1% to about 100% of b.

In certain preferred embodiments, each of $R_1$ and $R_2$ is methyl.

In certain preferred embodiments, each of $R_{L1}$ and $R_{L2}$ is selected from —$(CH_2)_m$—, wherein m is an integer from about 1 to about 15 (e.g., from about 1 to about 10, from about 1 to about 6, from about 1 to about 3, from about 3 to about 6, from about 3 to about 15), and —$(CH_2CH_2$—$O)_q$—, wherein q is an integer from about 1 to about 50 (e.g., from about 1 to about 30, from about 1 to about 20, from about 1 to about 10, from about 1 to about 6, from about 1 to about 3, from about 3 to about 10, from about 6 to about 20).

$R_F$ can be any suitable functional groups, for example, selected from the group consisting of amines, carboxylates, sulfates, sulfonates, phosphates, phosphonates, hydroxyl, halides, acyl halides, esters, azides, nitriles, amides, epoxides, aldehydes, furans, alkenes and alkynes.

In certain preferred embodiments, $R_F$ includes an amine group.

In certain preferred embodiments, $R_F$ includes an activated carboxylic ester group.

$R_x$ can be any crosslinking group group, for examples, selected from coumarin, alkenes, thiols, reactive disulfides, esters, reactive esters, maleimides, alkynes, furans, aldehydes and epoxides.

A unique aspect of the invention is that the molecular design involves self-assembly of amphiphilic random copolymers. In the aqueous phase, the surface functional groups of such an assembly would be dictated by the hydrophilic moiety of the polymer. Here, for example, the use of a primary amine based monomer as the hydrophilic moiety, combined with a reactive hydrophobic monomer as the crosslinkable moiety, led to a functionalizable polymer nanoparticle. The amphiphilic nature of the nano-assembly also allows for incorporation of guest molecules within the hydrophobic interior of the assembly prior to crosslinking. (FIG. 1)

Disclosed herein are the design, synthesis, characterization, and further functionalization of various functionalized polymeric nanoparticles. Primary amines are employed as examples of the surface functional groups. The reactivity of primary amines complements a wide range of functional groups such as alkyl halides, Michael acceptors, carboxylic acid, acid chlorides, activated esters, epoxides, anhydride and aldehydes.

Referring to Scheme 1, polymer 1, a poly(methacrylamide), is derived from the co-polymerization of 2-aminoethylmethacylamide and 3-(9-methylcoumarinoxy)propyl methacrylamide (Scheme 1). This co-polymer self-assembles into an amphiphilic aggregate, where the hydrophilic amino moieties are exposed to the aqueous phase, while the coumarin moieties are tucked in the hydrophobic interior. The propensity of coumarins to undergo photochemically driven [2+2] cylcoaddition reaction (Muthuramu, et al. 1982 *J. Org. Chem.* 47, 3976; Gnanaguru, et al. 1985 *J. Org. Chem.* 50, 2337-2346; He, et al. 2011 *Soft Matter*, 7, 2380-2386; Trenor, et al. 2004 *Chem. Rev.* 104, 3059-3078; Raghupathi, et al. 2011 *Chem. Eur. J.* 17, 11752-11760) was utilized to achieve the targeted polymer nanoparticles.

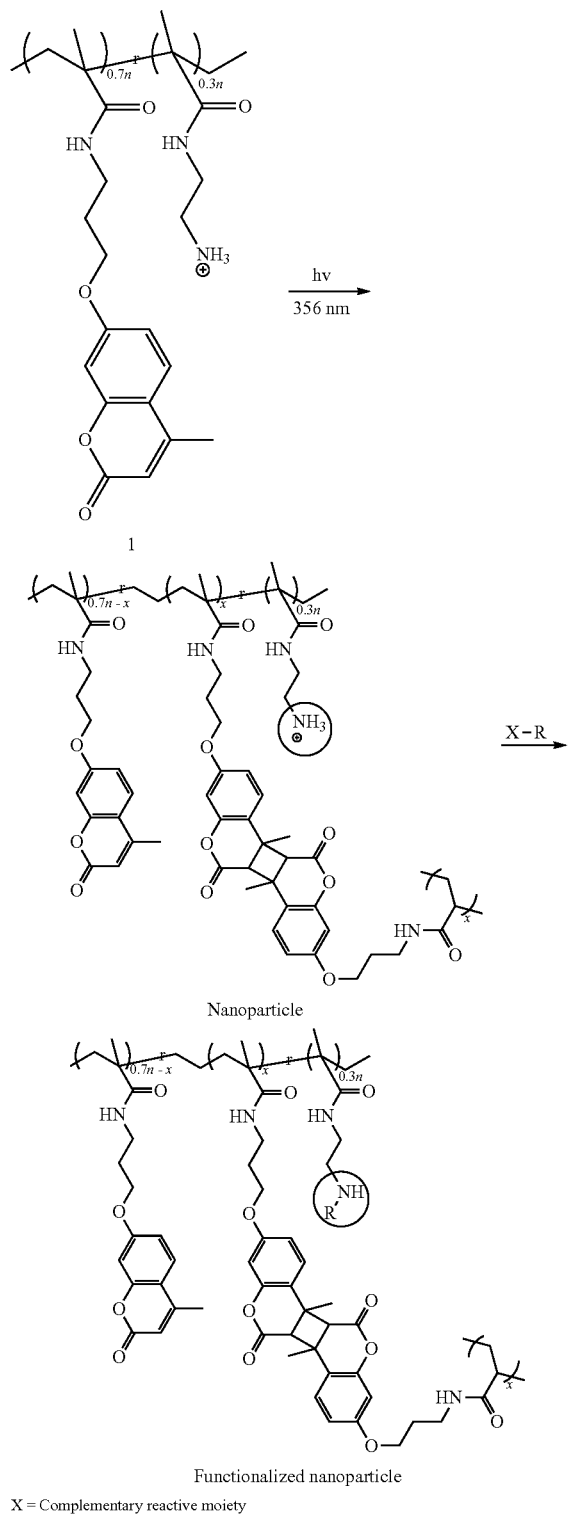

Scheme 1.
Synthesis of the polymer precursor and the nanoparticle

X = Complementary reactive moiety
R = New surface functionality

Figure 2:
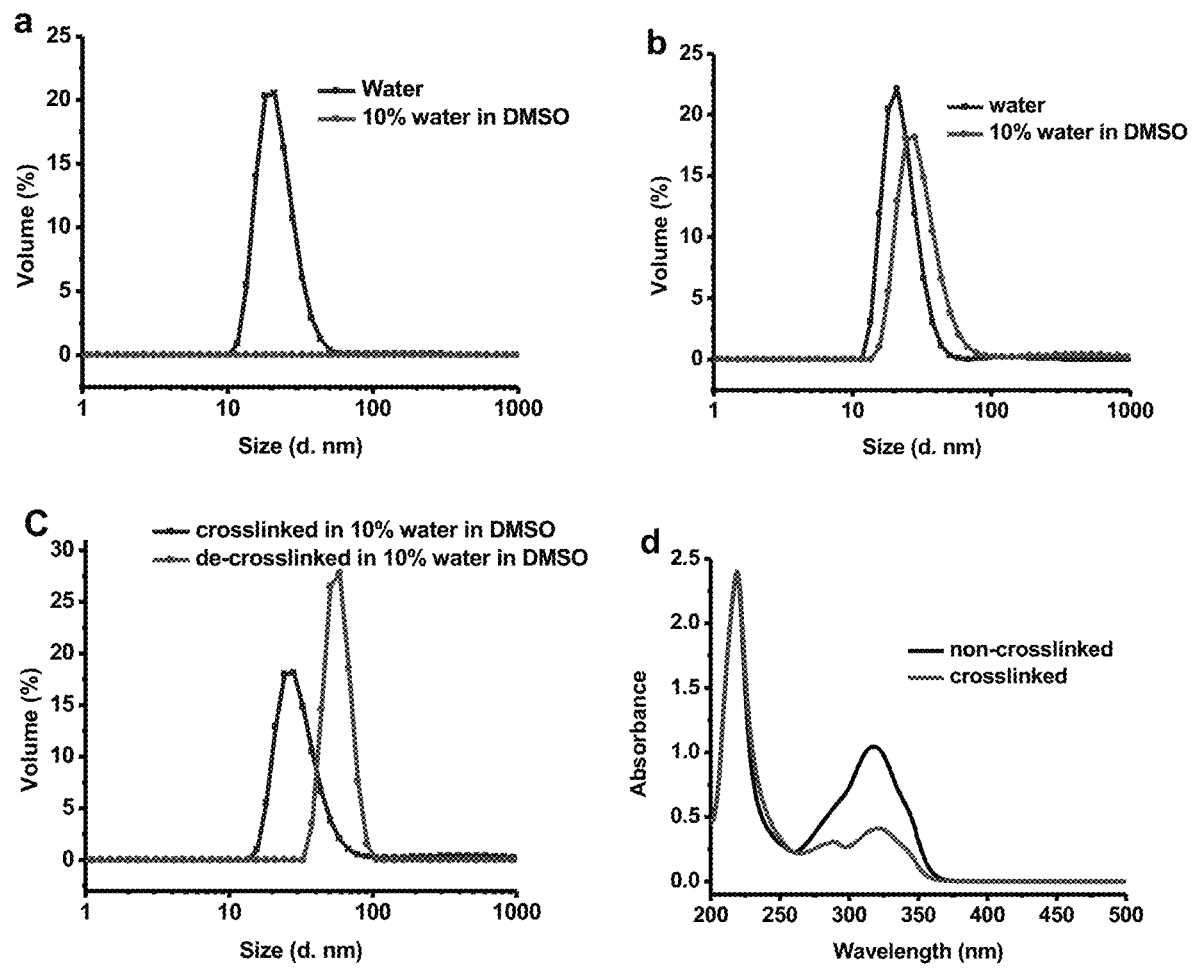
FIG. 2. Size distributions of (a) non-crosslinked, (b) cross-linked, and (c) de-crosslinked random copolymer 1 by DLS. (d) Absorption spectra of non-crosslinked and cross-linked random copolymer 1.

To synthesize the targeted polymer 1, the precursor random copolymer, which contains 30% of N-Boc-aminoethylmethacrylamide and 70% of 3-(9-methylcoumarinoxy)propylmethacrylamide was first synthesized; this polymer was prepared by reversible addition-fragmentation chain transfer (RAFT) polymerization. The Boc group was deprotected using trifluoroacetic acid in dichloromethane to yield the random copolymer 1. An aqueous solution of this polymer forms an aggregate of ~22 nm at 1 mg/mL concentration, as discerned by dynamic light scattering (DLS). This solution was then irradiated at 365 nm for 10 minutes to generate the crosslinked nanoparticle. Several features of this reaction are noteworthy: (i) the intensity of the absorption peak centered at 320 nm, which corresponds to the coumarin moiety, reduces within this irradiation time—confirming the photochemical reaction of the coumarin moiety; (ii) the size of the nanoparticle is the same as the aggregate, suggesting that the coumarin dimerization process is exclusively intra-aggregate—note that inter-aggregate reactions would result higher nanoparticle sizes; (iii) there is no discernible nanoaggregate of the uncrosslinked polymer in 10% water in DMSO, while the crosslinked nanoparticle's size is slightly increased in this solvent mixture (FIG. 2)—this swelling feature further confirms the crosslinked nature of the nanoparticle. The degree of swelling should inversely vary with the degree of crosslinking. It is known that irradiation of coumarin dimers at 250 nm causes it to revert to the monomer. (Muthuramu, et al. 1982 *J. Org. Chem.* 47, 3976; Gnanaguru, et al. 1985 *J. Org. Chem.* 50, 2337-2346; He, et al. 2011 *Soft Matter,* 7, 2380-2386; Trenor, et al. 2004 *Chem. Rev.* 104, 3059-3078; Raghupathi, et al. 2011 *Chem. Eur. J.* 17, 11752-11760). This reaction is often not complete because of the photostationary state between the monomer and the dimer at this irradiation wavelength. Therefore, this reaction should cause the crosslink density to lower. Accordingly, crosslinked nanoparticle in 10% water in DMSO was irradiataed at 250 nm for 30 minutes. DLS study of this solution indeed showed a further increase in size (FIG. 2).

Figure 3:
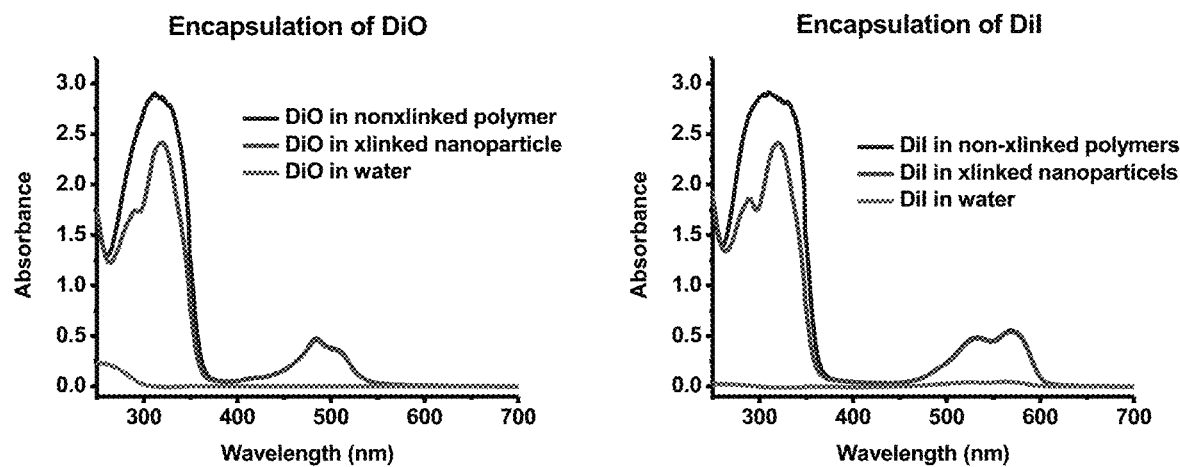
FIG. 3. Absorption spectra of guest molecules in non-crosslinked and crosslinked random copolymer 1.

Hydrophobic dye molecules, such as 1,1'-dioctadecyl-3,3,3',3'-tetramethylindocarbocyanine perchlorate (DiI) or 3,3'-dioctadecyloxacarbocyanine perchlorate (DiO) were encapsulated in the polymer aggregates successfully and guest molecules were retained in the interiors of nanoparticles after photoinduced crosslinking (FIG. 3).

Figure 4:
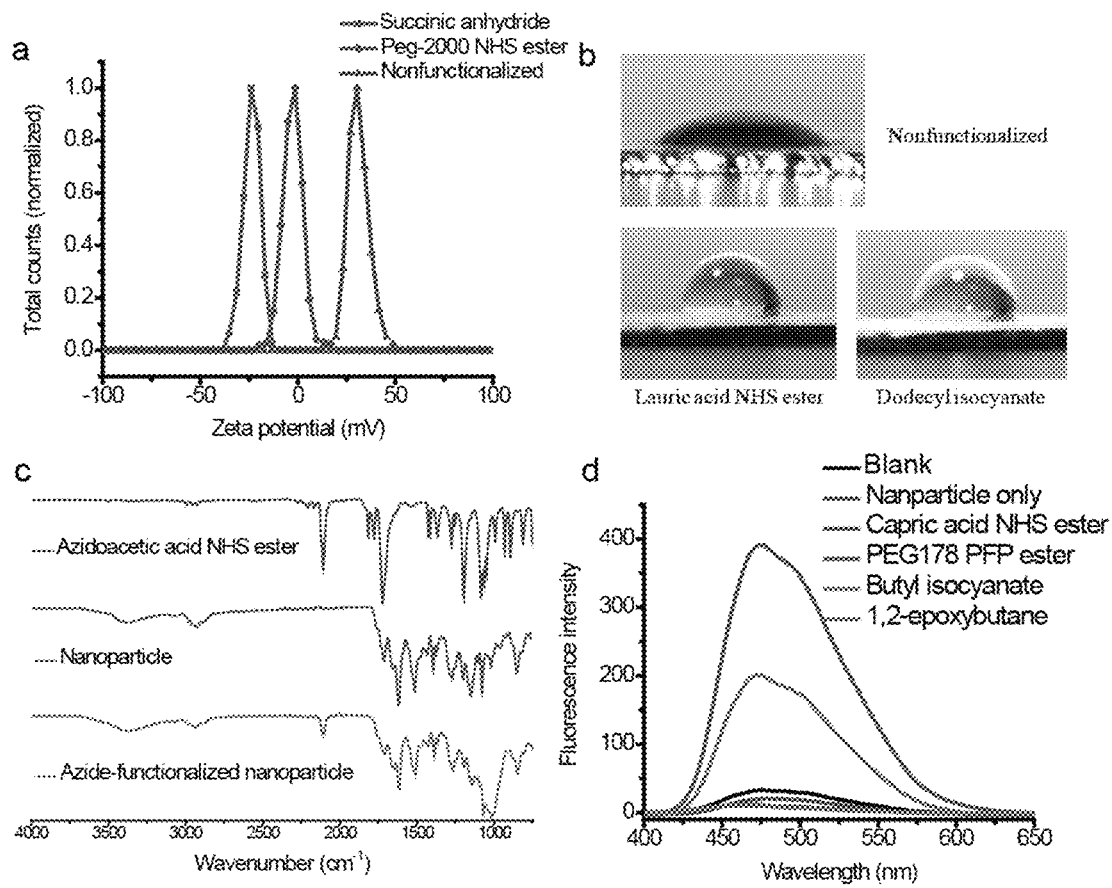
FIG. 4. (a) Surface charges of nanoparticles by zeta potential (b) Contact angle measurements of unmodified nanoparticles (top) and nanoparticles modified by lauric acid NHS ester (bottom left) and dodecyl isocyanate (bottom right). (c) IR spectra of azidoacetic acid NHS ester (top), unmodified nanoparticles (middle), and nanoparticles functionalized with azidoacetic acid NHS ester (bottom). (d) Fluorescence emission intensity of nanoparticles treated with excess fluorescamine after reacting with different functional groups.

The versatility of the amine functionality provides a ready handle for various surface functionalizations of the nanoparticles. First, amines were reacted with an activated ester and a cyclic anhydride to provide amides with complementary surface characteristics. Reaction of the amine-functionalized nanoparticles with a peg-2000 NHS ester converted the positively charged surface of the polymer nanoparticle to a charge neutral surface, while the reaction with succinic anhydride should convert the charge to negative. Zeta potential measurements of the reactants and the products confirmed surface charge modification (FIG. 4a).

Figure 5:
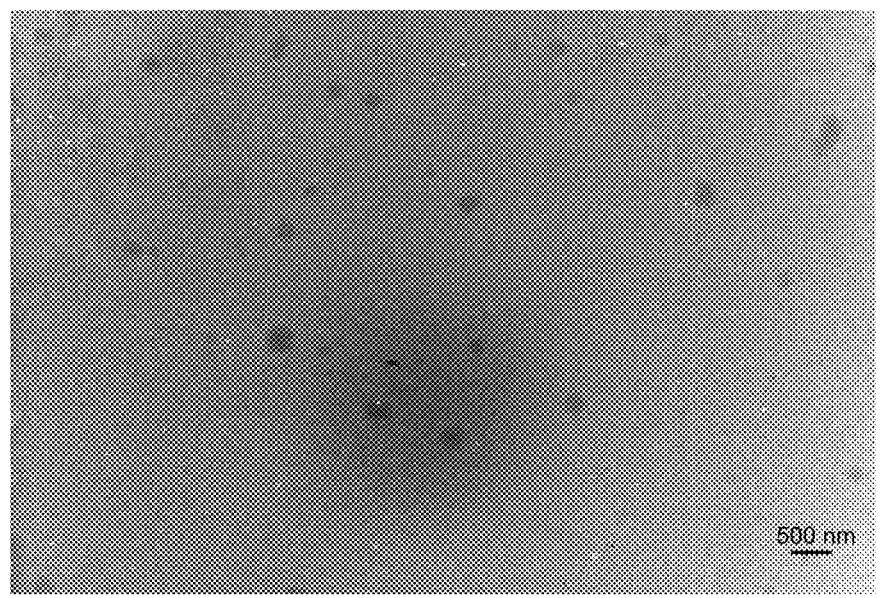
FIG. 5. Nanoparticles (~180 nm by DLS) functionalized with capric acid NHS ester (~190 nm by TEM).

Second, the nanoparticles were modified by a NHS ester (of lauric acid) and an isocyanate (dodecyl). The size of the nanoparticles stayed similar after modification, which was confirmed by TEM (FIG. 5). Both modifications would change the surface nanoparticles from hydrophilic to hydrophobic. Evaluation of the nanoparticle surface hydrophobicity by contact angle showed that the unmodified nanoparticles exhibited a contact angle of 33°, while the modified nanoparticles have a contact angle of 103° and 98°, respectively (FIG. 4b).

Next, the surface functionalization was monitored by FTIR. The nanoparticles were reacted with the NETS-ester of azidoacetic acid. The FTIR spectrum of modified nanoparticles showed the appearance of a peak at 2100 cm', characteristic of the azido group, with the concurrent disappearance of the NETS ester peaks at 1812 cm$^{-1}$ and 1783 cm$^{-1}$ (FIG. 4c). To directly analyze the conversion of the amino moiety on the nanoparticle surface, a well-established fluorescamine assay was used, in which selective reaction of primary amines with fluorescamine provides a fluorescent derivative. (Udenfriend, et al. 1972 Science 178, 871-872.)

The relative fluorescence was used to ascertain the extent of surface functionalization. Nanoparticles were first reacted with molecules with different amine-reactive functional groups (pentafluorophenol (PFP) ester, NHS ester, epoxide, and isocyanate). The extent of functionalization was analyzed by comparing the fluorescence from the functionalized amine nanoparticles and the unreacted amine nanoparticle. The fluorescence from three of the functionalized nanoparticles (PFP ester, NHS ester, and isocyanate) was found to be similar to that found with the negative control, indicating that the reaction was quantitative in these cases (FIG. 4d).

Experiments were performed to investigate the tuning of the nanoparticle sizes. While variations such as polymer MW, concentration, and monomer ratio could afford different aggregate sizes, a simpler variation with the same polymer was also studied as a way to tune the nanoparticle sizes.

Figure 6:
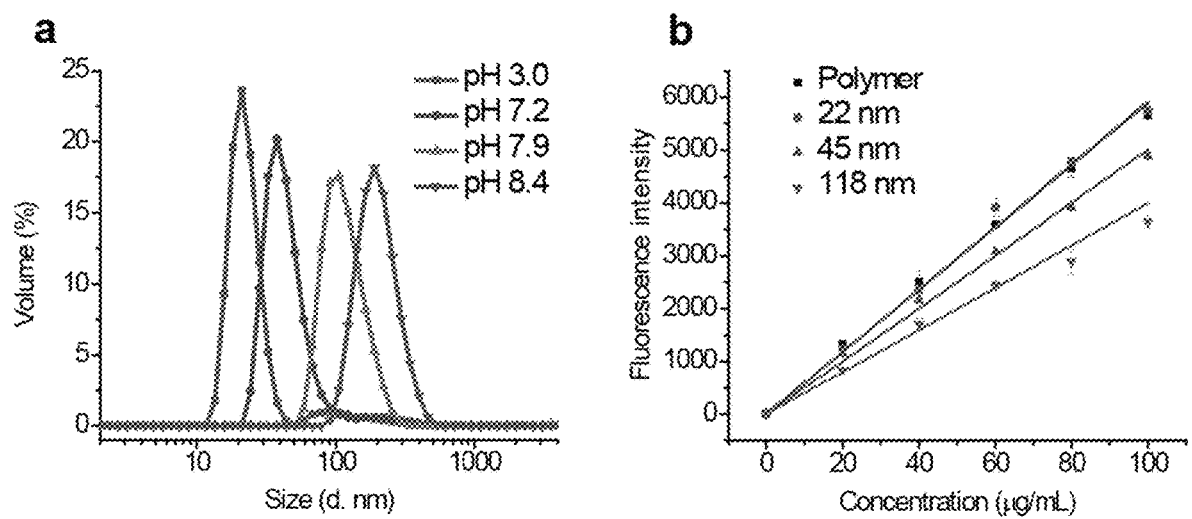
FIG. 6. (a) Size distribution of nanoparticles cross-linked at different pHs in water. The DLS measurements were all done at pH 3. (b) Percentage of amine available for functionalization on different nanoparticle sizes accessed by fluorescamine assay.

The pH of the solution and the ensuing variation the hydrophilic-lipophilic balance of the polymer was studied. Aqueous solutions of polymer 1 at different pH were prepared. The polymer precipitates out at pH~9, consistent with the pK$_a$ of amine groups. Also observed was that the aggregate sizes were not significantly different between pH 3.0 and 6.5. Interestingly, the greatest size differences were observed with subtle pH changes between 7.0 and 8.5, indicating that subtle changes in the degree of protonation of the amines lead to significant size differences. This is presumably due to the difference in hydrophilic lipophilic balance of the polymer at these pHs. These differences can be utilized to systematically tune the size of the nanoparticles by photochemically locking these aggregates, as shown in FIG. 6a.

Although the fluorescamine assay showed that all the accessible amines can be utilized for surface decoration, it is important to investigate the percentage of amines in the polymer nanoparticle that are inherently accessible. Fluorescamine assay was carried out in 1:3 water/DMSO mixture, in which no aggregation was observed for the non-cross-linked polymer. The fluorescence generated from the uncrosslinked polymer was utilized as a true indicator of the amine moieties available in the polymer. Evaluation of nanoparticles of different sizes, using this as the standard, indicated that nearly all the amine moieties seem to be available at a particle size of 22 nm. However, only 85% and 65% of the amine moieties were available for functionalization in 45 nm and 118 nm particles respectively (FIG. 6b). This supports the notion that the smaller surface area of larger nanoparticles leads to decreased availability of surface functionalities.

Thus, the versatile polymer nanoparticles provide a number of key advantages as they (i) display versatile functional groups on its surface, which can be further manipulated with a variety of complementary reactive moieties; (ii) are capable of non-covalently binding hydrophobic guest molecules; (iii) afford size tunability by simply altering the pH at which the nanoparticle is synthesized; (iv) have a very high percentage of the accessible surface moieties at smaller sizes. Overall, the simplicity and versatility of the surface functionalizable soft nanoparticles with host-guest capabilities have implications in a variety of applications from materials to biology.

EXPERIMENTAL

Materials and Methods

All chemicals and reagents were purchased from commercial sources and were used as received, unless otherwise mentioned. $^1$H-NMR spectra were recorded on a 400 MHz Bruker NMR spectrometer using the residual proton resonance of the solvent as the internal standard. $^{13}$C-NMR spectra were recorded on a 400 MHz Bruker NMR spectrometer using carbon signal of the deuterated solvent as the internal standard. $^{19}$F-NMR spectra were collected on a 300 MHz Bruker NMR spectrometer. Molecular weights of the polymers were estimated by gel permeation chromatography (GPC) using PMMA standard with a refractive index detector. Dynamic light scattering (DLS) and zeta potential were determined by Nano-ZS (Malvern Instrument) Zetasizer. The fluorescence spectra were obtained from a JASCO FP-6500 spectrofluorimeter. UV-visible absorption spectra were collected using a Cary 100 spectrophotometer. FTIR spectra were recorded on a Perkin Elmer spectrometer. Contact angles of water were examined on a Ramé-Hart telescopic goniometer. Transmission electron microscopy (TEM) images were taken from JEOL 100CX at 100 KV.

Synthetic Methodologies

Synthesis of N-2-[(tert-butoxycarbonyl)amino]ethyl Methacrylamide (Boc-AEMA)

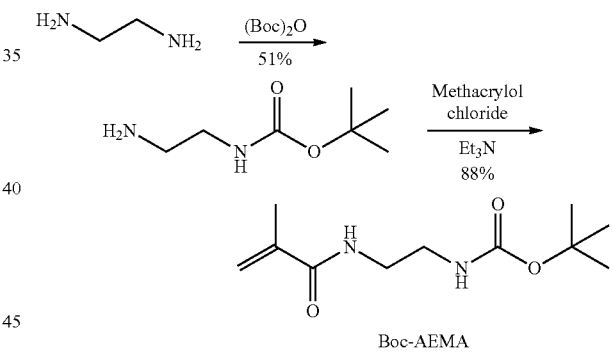

Synthesis of 4-Methylcoumarin-7-oxypropyl Methacrylamide (CPMA)

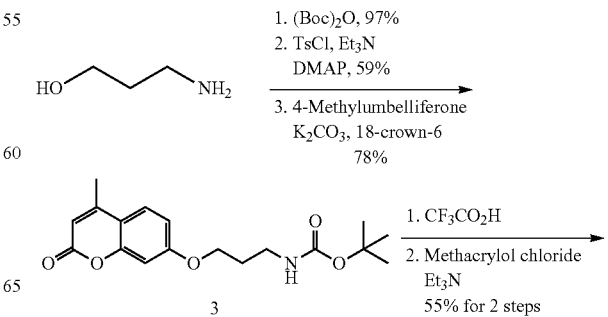

15

-continued

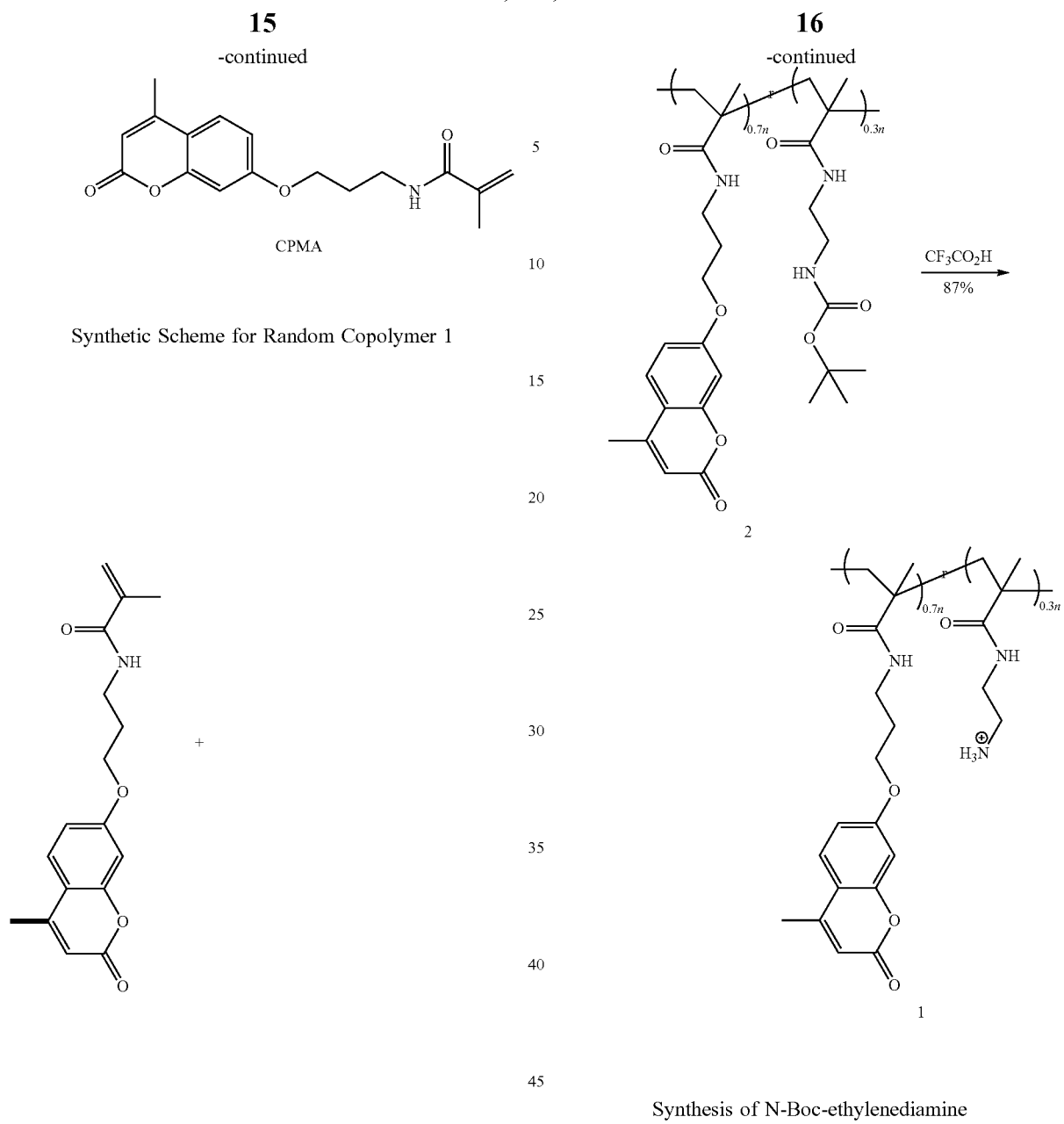

Synthetic Scheme for Random Copolymer 1

16

-continued

Synthesis of N-Boc-ethylenediamine

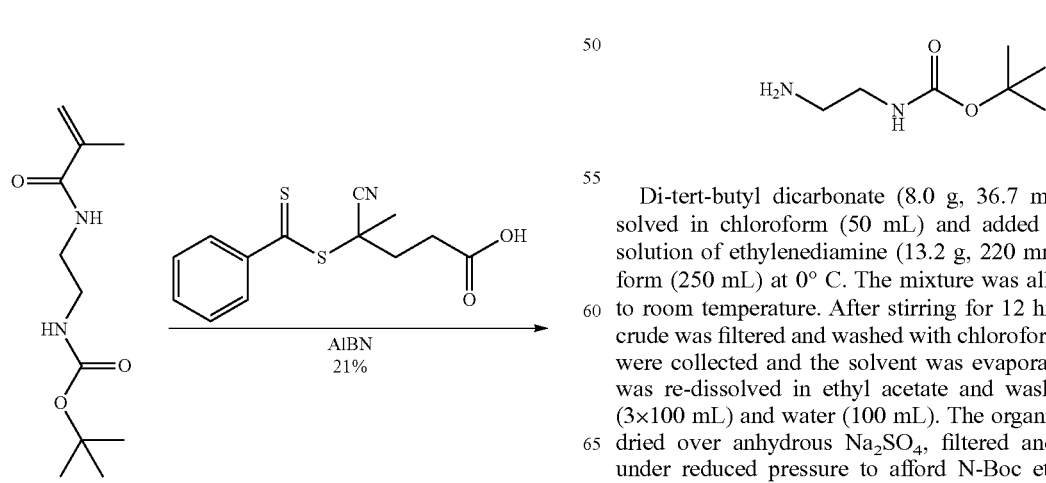

Di-tert-butyl dicarbonate (8.0 g, 36.7 mmol) was dissolved in chloroform (50 mL) and added dropwise to a solution of ethylenediamine (13.2 g, 220 mmol) in chloroform (250 mL) at 0° C. The mixture was allowed to warm to room temperature. After stirring for 12 hrs, the reaction crude was filtered and washed with chloroform. The filtrates were collected and the solvent was evaporated. The crude was re-dissolved in ethyl acetate and washed with brine (3×100 mL) and water (100 mL). The organic solution was dried over anhydrous $Na_2SO_4$, filtered and concentrated under reduced pressure to afford N-Boc ethylenediamine (2.97 g, 51%) as a colorless oil. $^1$H NMR (400 MHz, $CDCl_3$)

δ: 4.95 (bs, 1H), 3.20 (q, 2H), 2.82 (t, 2H), 1.99 (s, 2H). (Roy, et al. 2012 *ACS Macro Lett.* 1, 529-532.)

Synthesis of N-2-[(tert-butoxycarbonyl)amino]ethyl methacrylamide (Boc-AEMA)

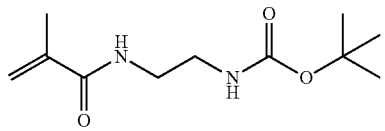 [SMILES: C=C(C)C(=O)NCCNC(=O)OC(C)(C)C]

To a solution of N-Boc-ethylenediamine (2.0 g, 12.5 mmol) in 20 mL of dry dichloromethane was added 1.5 g (15.0 mmol) of triethylamine and the mixture was cooled in an ice-bath. To this cold mixture, a solution of methacryloyl chloride (1.3 g, 12.5 mmol) in 10 mL dichloromethane was added dropwise with continuous stirring. After the addition, the reaction mixture was stirred at room temperature for 6 hr. The stirring was stopped and the reaction mixture was washed with 3×30 mL distilled water and then with 30 mL of brine. The organic layer was collected, dried over anhydrous $Na_2SO_4$ and concentrated to get the crude product as a white solid. It was purified by column chromatography using silica gel as stationary phase and mixture of ethyl acetate/hexane as eluent. Yield: 2.52 g (88%). $^1$H NMR (400 MHz, $CDCl_3$) δ: 6.70 (bs, 1H), 5.75 (s, 1H), 5.33 (s, 1H), 4.92 (bs, 1H), 3.41 (q, 2H) 3.33 (q, 2H), 1.96 (s, 3H), 1.44 (s, 9H). (Sun, et al. 2007 *Chem. Eur. J.* 13, 7701-7707.)

Synthesis of Compound 3a

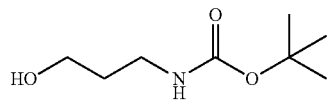

To a solution of 3-aminopropanol (2.0 g, 26.6 mmol) in chloroform (50 mL) was added di-tert-butyl dicarbonate (7.0 g, 31.9 mmol) at 0° C. and stirred for 6 hrs at room temperature. Chloroform was evaporated and the residue was re-dissolved in ethyl acetate and washed with saturated $NaHCO_3$ aqueous solution (100 mL) and brine (2×100 mL) The organic solution was dried over anhydrous $Na_2SO_4$, filtered and concentrated in vacuo to afford N-boc-3-aminopropanol (4.5 g, 97% yield). $^1$H NMR (400 MHz, $CDCl_3$) δ: 3.66 (t, 2H), 3.29 (t, 2H), 1.66 (p, 2H), 1.44 (s, 9H). (Mehlich, et al. 2011 *Org. Biomol. Chem.* 9, 4108-4115.)

Synthesis of compound 3b

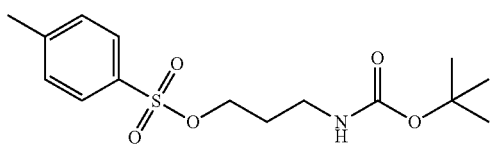 [SMILES: Cc1ccc(S(=O)(=O)OCCCNC(=O)OC(C)(C)C)cc1]

N-boc-3-aminopropanol (4.0 g, 22.8 mmol) was dissolved in 100 mL of dry dichloromethane and 2.7 g (27.4 mmol) of triethylamine was added to it. To this mixture, a solution of p-toluenesulfonyl chloride (5.2 g, 27.4 mmol) and 4-dimethylaminopyridine (catalytic amount) in 20 mL dry dichloromethane was added. The reaction mixture was allowed to stir at room temperature overnight. Solvent was evaporated to get the crude product, which was purified by flash column chromatography using silica gel as stationary phase and mixture of ethyl acetate/hexane as eluent. Yield: 4.46 g (59%). $^1$H NMR (400 MHz, $CDCl_3$) δ: 7.80 (d, 2H), 7.36 (d, 2H), 4.10 (t, 2H), 3.16 (t, 2H), 2.45 (s, 3H), 1.84 (p, 2H), 1.42 (s, 9H). (Simoni, et al. 2012 *J. Med. Chem.* 55, 9708-9721.)

Synthesis of compound 3

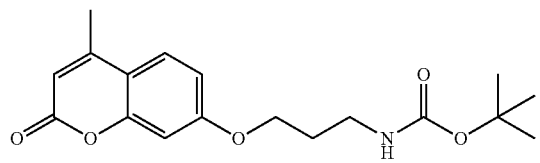 [SMILES: Cc1cc(=O)oc2cc(OCCCNC(=O)OC(C)(C)C)ccc12]

In a two-neck round bottom flask, compound 3b (3.0 g, 9.1 mmol) was mixed with 4-methylumbelliferone (1.76 g, 10.0 mmol), $K_2CO_3$ (1.38 g, 10.0 mmol), and 18-crown-6 (0.48 g, 1.82 mmol) in acetone (300 mL) under argon atmosphere. The reaction mixture was refluxed for 12 hours. Then, the crude reaction mixture was filtered and washed with acetone. The filtrates were collected and the solvent was evaporated. The crude was then poured into water and extracted with ethyl acetate (3×100 mL). The organic layers were dried over anhydrous $Na_2SO_4$, filtered, and concentrated in vacuo. The crude product was purified by flash column chromatography using silica gel as stationary phase and mixture of ethyl acetate/hexane as eluent. Yield: 2.36 g (78% yield). $^1$H NMR (400 MHz, $CDCl_3$) δ: 7.48 (d, 1H), 6.84 (dd, 1H), 6.80 (d, 1H), 6.13 (s, 1H), 4.73 (bs, 1H), 4.07 (t, 2H), 3.34 (q, 2H), 2.39 (s, 3H), 2.01 (p, 2H), 1.44 (s, 9H). $^{13}$C NMR (400 MHz, $CDCl_3$) δ: 162.0, 161.5, 156.1, 155.4, 152.7, 125.7, 113.8, 112.7, 112.2, 101.58, 79.8, 66.3, 38.0, 29.7, 28.5, 18.8.

Synthesis of 4-Methylcoumarin-7-oxypropyl methacrylamide (CPMA)

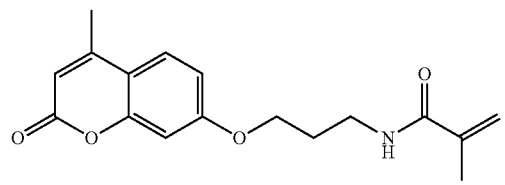 [SMILES: C=C(C)C(=O)NCCCOc1ccc2c(C)cc(=O)oc2c1]

To deprotect the N-boc amine functionality, compound 3 (2.36 g, 7.1 mmol) was dissolved in 10 mL of 1:1 v/v dichloromethane/trifluoroacetic acid mixture. After stirring at room temperature for 2 hrs, solvent mixture was removed by evaporation, and the oil residue was rinsed two times with diethyl ether (20 mL). The resultant precipitate was collected and dried in vacuo. To a solution of the dried precipitate in 50 mL of dry dichloromethane was added 2.15 g (21.3 mmol) of triethylamine and the mixture was cooled in an ice-bath. To this cold mixture, a solution of methacryloyl chloride (0.82 g, 7.8 mmol) in 10 mL dichloromethane was added drop-wise with continuous stirring. After the addition, the reaction mixture was stirred at room temperature for 6 hrs. The reaction mixture was then washed with 3×30 mL distilled water and then with 30 mL of brine. The organic layer was collected, dried over anhydrous $Na_2SO_4$ and concentrated to get the crude product as a yellow solid. It was purified by column chromatography using silica gel as stationary phase and mixture of ethyl acetate/hexane as eluent. Yield: 1.18 g (55%). $^1$H NMR (400 MHz, $CDCl_3$) δ: 7.50 (d, 1H), 6.84 (dd, 1H), 6.80 (d, 1H), 6.19 (bs, 1H), 6.14 (s, 1H), 5.71 (s, 1H), 5.34 (s, 1H), 4.12 (t, 2H), 3.55 (q, 2H), 2.39 (s, 3H), 2.10 (p, 2H), 1.97 (s, 3H); $^{13}$C NMR (400 MHz, $CDCl_3$) δ: 168.7, 161.8, 161.4, 155.3, 152.7, 140.0, 125.7, 119.8, 113.8, 112.4, 112.1, 101.6, 67.0, 37.5, 28.9, 18.8.

Synthesis of Random Copolymer 1

A mixture of 4-cyano-4-(phenylcarbonothioylthio)pentanoic acid (7.8 mg, 0.028 mmol), Boc-AEMA (194 mg, 0.85 mmol), CPMA (600 mg, 1.99 mmol) and AIBN (0.92 mg, 0.0019 mmol) was dissolved in DMF (10 ml) and degassed by performing three freeze-pump-thaw cycles. The reaction mixture was sealed and then heated with a preheated oil bath at 75° C. for 12 h. The resultant mixture was precipitated in ethyl acetate (200 mL) to remove unreacted monomers. The precipitate was further dissolved in dichloromethane (5 mL) and re-precipitated in ethyl acetate (200 mL) to yield purified random copolymer as a yellow solid. Yield: 21%. $^1$H NMR (400 MHz, $CDCl_3$/MeOD) δ: 6.8-7.4, 6.5-6.8, 5.8-6.0, 3.8-4.1, 3.0-3.4, 2.1-2.4, 1.5-2.0, 1.2-1.4, 0.7-1.2. GPC (THF) $M_n$: 3000 Da. PDI: 1.3. The molar ratio between two blocks was determined by integrating the Boc group protons in Boc-AEMA and an aromatic proton in the coumarin and found to be 3:7 (Boc-AEMA:CPMA). To remove the Boc groups, the resulting random copolymer was dissolved in 10 mL of 1:1 v/v trifluoroacetic acid/dichloromethane mixture and stirred overnight at room temperature. Solvent mixture was then removed by evaporation, and the oil residue was rinsed three times with diethyl ether. The resultant precipitate was collected and dried overnight in vacuum to afford random copolymer 1. Yield: 87%. $^1$H NMR (400 MHz, DMSO-d6) δ: 7.3-8.2, 6.7-7.1, 6.0-6.2, 3.9-4.2, 3.0-3.3, 2.7-2.9, 2.2-2.4, 1.5-2.1, 0.7-1.2. Complete disappearance of the methyl proton signal of the Boc group at 1.2-1.4 ppm confirmed that all the Boc groups have been removed.

Synthesis of Azidoacetic Acid

To a solution of sodium azide (2.3 g, 36 mmol) in water (50 mL) was added bromoacetic acid (1.0 g, 7.2 mmol) slowly. The reaction mixture was stirred overnight at room temperature. The reaction was quenched with 1 M of HCl aqueous solution. The crude material was mixed with water (50 mL) and extracted with ethyl acetate (3×100 mL). The organic solution was dried over anhydrous $Na_2SO_4$, filtered and concentrated under reduced pressure to afford azidoacetic acid (0.39 g, 54% yield). $^1$H NMR (400 MHz, $CDCl_3$) δ: 10.62 (bs, 1H), 3.98 (s, 2H). (Ghosh, et al. 2012 Chem. Eur. J. 18, 2361-2365.)

Synthesis of [2-(2-methoxyethoxy)ethoxy]acetic acid pentafluorophenyl ester (Peg178 PFP ester)

To a solution of [2-(2-methoxyethoxy)ethoxy]acetic acid (1 equivalent) and pentafluorophenol (1.2 equivalent) in dry dichloromethane was added 1-(3-dimethylaminopropyl)-3-ethylcarbodiimide hydrochloride (1.2 equivalent) and catalytic amount of 4-dimethylaminopyridine at 0° C. The reaction mixture was stirred for 6 h at room temperature. The reaction mixture was washed with saturated $NaHCO_3$ aqueous solution and then with brine. The organic solution was dried over anhydrous $Na_2SO_4$, filtered and concentrated under reduced pressure to afford the crude product. It was purified by column chromatography using silica gel as the stationary phase and mixture of ethyl acetate/hexane as eluent. Yield: 50%. $^1$H NMR (400 MHz, $CDCl_3$) δ: 4.54 (s, 2H), 3.83 (m, 2H), 3.74 (m, 2H), 3.65 (m, 2H), 3.57 (m, 2H), 3.38 (s, 3H). $^{19}$F NMR (300 MHz, $CDCl_3$) δ: −152.5 (2F), −157.3 (1F), −161.9 (2F).

General Procedure for the Synthesis of N-hydroxysuccinimide (NHS) Ester

To a solution of carboxylic acid (1 equivalent) and N-hydroxysuccinimide (1.2 equivalent) in dry dichloromethane was added 1-(3-Dimethylaminopropyl)-3-ethylcarbodiimide hydrochloride (1.2 equivalent) at 0° C. and stirred for 12 hours at room temperature. The stirring was stopped and the reaction mixture was washed with saturated $NaHCO_3$ aqueous solution and then with brine. The organic solution was dried over anhydrous $Na_2SO_4$, filtered and concentrated under reduced pressure to afford the N-hydroxysuccinimide ester.

Methoxypolyethylene Glycol 2,000 Acetic Acid NHS Ester (PEG2000 NHS Ester):

Synthesis of PEG2000 NHS ester was done in dry DMF and the crude reaction mixture was directly taken to next step without any purification.

Azidoacetic Acid NHS Ester:

Yield: 61%. $^1$H NMR (400 MHz, $CDCl_3$) δ: 4.24 (s, 2H), 2.88 (s, 4H). (Ghosh, et al. 2012 Chem. Eur. J. 18, 2361-2365)

Lauric Acid NHS Ester:

Yield: 71%. $^1$H NMR (400 MHz, $CDCl_3$) δ: 2.84 (s, 4H), 2.60 (t, 2H), 1.74 (p, 2H), 1.40 (p, 2H), 1.20-1.35 (m, 14H), 0.88 (t, 3H). (Kapdi, et al. 2013 New J. Chem. 37, 961-964)

Capric Acid NHS Ester:

$^1$H NMR (400 MHz, $CDCl_3$) δ: 2.84 (s, 4H), 2.60 (t, 2H), 1.74 (p, 2H), 1.17-1.48 (m, 12H), 0.88 (t, 3H). (Schulze, et al. 2004 Adv. Synth. Catal. 346, 252-256)

Encapsulation of Guest Molecules:

50 μL of 1 mg/mL DiO/DiI (in acetone) was added to a vial, followed by evaporating the acetone with mild blow of air. To this was added 2 mL of nanoparticle solution (1 mg/mL) and sonicated at room temperature for 2 hrs. The resultant mixture was then passed through 0.22 μm filter to remove the non-encapsulated DIO/DiI, followed by stirring the solution at room temperature overnight to remove any residual acetone present in the solution. This stock solution was accordingly diluted with milliQ water (pH 3) to achieve required concentration of the nanoparticles.

General Procedures for Surface Charge, Contact Angle and FTIR Measurements

To 1 mL of nanoparticle stock solution (1 mg/mL) at basic pH was added the functionalization agents (10 equivalents) dissolved in DMF. After stirring overnight at room temperature, the excess functional group reagents were removed by dialysis. For the functionalization with succinic anhydride, the reaction was done in 0.1 M NaCl solution to minimize the aggregation of opposite charge nanoparticles that could prevent the reaction from going to completion.

Surface Charge Measurements:

The reaction mixtures were first dialyzed in acetone to remove excess reagents and then were switched to aqueous medium. Solutions after dialysis were accordingly diluted with milliQ water to achieve a final concentration of 0.35 mg/mL. All solutions were adjusted to pH 7.1 and then filtered through a 0.22 µm filter before performing surface charge measurements.

Contact Angle Measurements:

To prepare samples for contact angle measurements, stock solution of nanoparticles dissolved in water and dodecyl-functionalized nanoparticles dissolved in dichloromethane were dropped onto a silicon slides and dried at room temperature overnight.

Functionalization of Nanoparticles for Emission Spectrum Measurements

Emission spectra were recorded on a JASCO (FP-6500) spectrofluorimeter using quartz cuvettes. To 100 µL of nanoparticle (1 equivalent) stock solution at basic pH, functional groups (3 equivalents) dissolved in DMSO (800 µL) were added and stirred overnight at room temperature. Fluorescamine (10 equivalents) dissolved in DMSO (100 µL) was then added and stirred for another 2 h at room temperature. All solutions were directly taken to the spectrofluorimeter for measurement without further purification. The emission spectra for fluorescamine-amine adduct were recorded by exciting at 390 nm, with both excitation and emission bandwidths set at 3 nm.

Quantifying the Amounts of Amine Available for Functionalization

Different aliquots of nanoparticle (200 µg/mL) were pipetted into a 96 well microplate in triplicates. Different volumes of water and DMSO were added to adjust the final water/DMSO (1:2, v:v) volume to 150 µL. The microplate was placed on a microplate shaker and 50 µl of 3.6 mM (1 mg/mL) fluorescamine dissolved in DMSO was added to each well. Following the addition of fluorescamine the plate was shaken for one minute and then allowed to stand at room temperature for 2 h. The fluorescence was then determined using a SpectraMax M5 plate reader with a 400 nm excitation filter and a 460 nm emission filter. The sensitivity setting was at 6 and the data collected from the top.

Different Percentage of Amines on the Nanoparticles can be Functionalized

Figure 7:
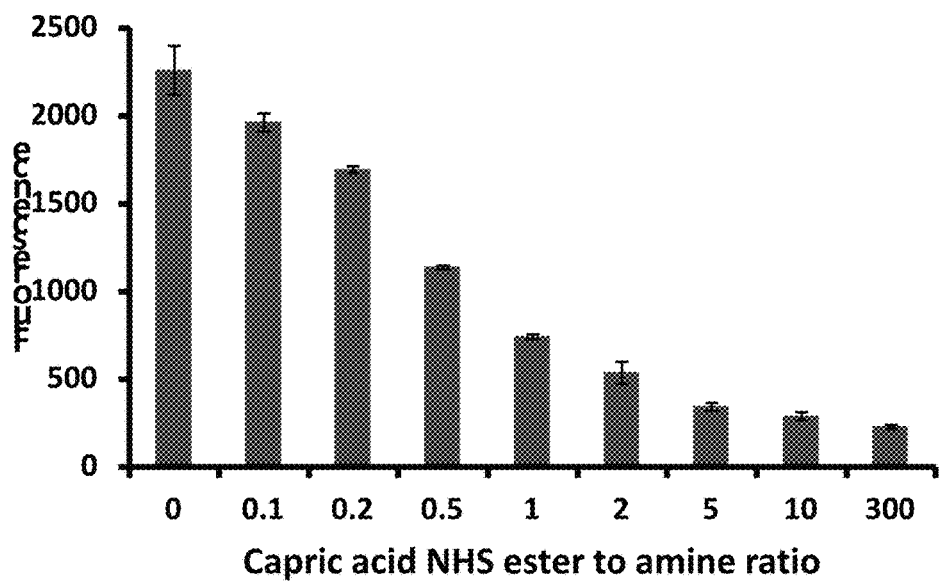
FIG. 7. Nanoparticles reacted with different concentrations of capric acid NHS ester monitored by fluorescamine.

100 µL aliquots of nanoparticle (200 µg/mL) were pipetted into a 96 well microplate in triplicates, followed by addition of different equivalents of capric acid NHS ester dissolved in DMSO to each well. Different volumes of water and DMSO were added accordingly to adjust the final water/DMSO (1:2, v:v) volume to 150 µL. The microplate was allowed to stay at room temperature for 6 hours during which it was shaken on a microplate shaker for the frequency of one minute per hour (FIG. 7).

Size Control 2 mL polymer solutions (1 mg/mL) in scintillation vials were adjusted to the required pH using NaOH and HCl aqueous solution. After sonicating for 2 min, all solutions were irradiated under UV light (365 nm) for 10 min to crosslink the polymers. The nanoparticle solutions were dialyzed in milliQ water to remove residual DMSO. All nanoparticle solutions were adjusted to pH 3 and then filtered through a 0.22 µm filter before performing dynamic light scattering measurements.

II. Surface-Functionalized Polymer Nanoparticles Self-Assembled from Amphiphilic Homopolymers Amphiphilic homopolymers have been shown to have predictable solution self-assembly behavior and applications in peptide extraction and guest delivery. Although it is relatively easily to homopolymerize an amphiphilic monomer, the multistep synthesis of monomer itself is laborious. A new methodology with a simple polymer preparation is strongly desired that can profoundly enhance the application of amphiphilic polymers.

In yet another aspect, the invention generally relates to a polymer-based nanoparticle having vesicular structures stabilized by intraparticular crosslinking, wherein the polymer is an amphiphilic homopolymer comprising a hydrophilic head group and a hydrophobic tail group.

In certain embodiments, the hydrophilic head group is selected from charged functional groups such as amino, ammonium, sulfonium, phosphonium, carboxylate, phosphate, phosphonate, sulfate, and sulfonate groups and charge-neutral functional groups such as carboxy betaine, sulfo betaine, phosphoryl choline, phosphonyl choline, saccharides, and polyethylene glycol groups and the hydrophobic tail group is selected from linear and branched alkyl chains, linear and branched fluoro-substituted alkyl chains, and alkyl chains containing aromatic or heteromatic functional groups In certain embodiments, the intraparticular crosslinking is via a group selected from pyrdinyl disulfide, activated esters, coumarin derivatives, alkynes or alkenes along with thiols, maleimdes with thiols, amines and epoxides, amines, thiols or alcohols along with perforophenyl esters, and alkynes along with azides. In certain embodiments, the amphiphilic homopolymer is a cationic homopolymer. In certain embodiments, the cationic homopolymer includes one or more groups selected from amino, ammonium, sulfonium, phosphonium, pyridinium, imidazolium and other heteroaromatic cationic functional groups. In certain embodiments, the amphiphilic homopolymer is an anionic homopolymer. In certain embodiments, the anionic homopolymer includes one or more groups selected from carboxylate, phosphate, phosphonate, sulfate, and sulfonate groups. In certain embodiments, the amphiphilic homopolymer is a charge-neutral homopolymer. In certain embodiments, the charge-neutral homopolymer is selected from carboxy betaine, sulfo betaine, phosphoryl choline, phosphonyl choline, saccharides, and polyethylene glycol groups.

In certain embodiments, the nanoparticle is surface functionalized. In certain embodiments, the nanoparticle comprises one or more surface functional groups, for example, selected from the group consisting of amines, carboxylates, hydroxyl, halides, acyl halides, esters, azides, nitriles, amides, epoxides, aldehydes, furans, alkenes and alkynes. In certain embodiments, the surface functionalization results in the surface being functionalized by one or more groups selected from polyethylene glycol, amines, carboxylates, epoxides, activated esters, thiols, dopamines, and zwitterionic functional groups. In certain embodiments, the surface functionalization results in the surface being functionalized by peptides (including proteins and antibodies), nucleic acids (including aptamers), and small or large molecule ligands (including targeting ligands with desired binding specificity and selectivity).

In certain embodiments, the intraparticular crosslinking of the polymer-based nanoparticle is addressable by a biological or chemical intervention resulting in partial or complete disassembly of the polymer-based nanoparticle. In certain embodiments, the biological or chemical intervention is a change in pH, redox reagent, redox potential, ionic strength, enzymatic activity, protein concentration, light, heat, or mechanical stress.

In yet another aspect, the invention generally relates to a nano-assembly. The nano-assembly includes: a host crosslinked polymer-based nanoparticle disclosed herein; and a guest molecular cargo non-covalently encapsulated in the host crosslinked polymer-based nanoparticle. The host crosslinked polymer network is addressable by a biological or chemical intervention resulting in partial or complete decrosslinking of the host polymer network and release of the guest molecular cargo from the nano-assembly.

In certain preferred embodiments, the nano-assembly is a nanogel. In certain embodiments, the non-covalently encapsulated guest agent accounts for from 0.1 wt % about to about 45 wt % of the nanoparticle. In certain embodiments, the guest molecular cargo is selected from a therapeutic, diagnostic or imaging agent. In certain embodiments, the guest molecular cargo is a small molecule. In certain embodiments, the guest molecular cargo is a peptide (e.g., a polypeptide, a protein, an antibody). In certain embodiments, the molecular cargo is an oligonucleotide (e.g., DNA or RNA). In certain embodiments, the molecular cargo is an antitumor agent.

In yet another aspect, the invention generally relates to a method for forming a polymer-based nanoparticle disclosed herein. The method includes: providing an amphiphilic homopolymer by a ring opening reaction; causing self-assembly of the amphiphilic homopolymer, induced or assisted by one or more salt, to form a polymersome comprising vesicle structures; and performing an intraparticular crosslinking on the polymersome resulting in intramolecularly crosslinked polymer-based nanoparticle having vesicle structures.

Any suitable salt may be used to induce or assist the formation of the polymersome. In certain embodiments, the salt is one or more of $Na_2SO_4$, $Na_2S_2O_3$, and $Na_2SO_3$, $Na_2HPO_4$, $Na_3PO_4$, and similar multivalent anions with various counterions. In certain embodiments, the salt is one or more of $MgCl_2$, $CaCl_2$, $BaCl_2$, $BeCl_2$, $ZnCl_2$, $CuCl_2$, $BiCl_3$, and similar multivalent cations with various counterions.

In yet another aspect, the invention generally relates to a method for controlled delivery of a molecular cargo to a target biological site. The method includes: providing a nano-assembly disclosed herein; delivering the nano-assembly to the target biological site; and causing a biological or chemical intervention resulting in a partial or complete decrosslinking resulting in release of the guest molecular cargo from the nano-assembly.

In certain preferred embodiments, the homopolymer has the formula of

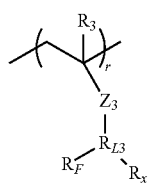

wherein $Z_3$ is

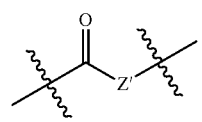

wherein Z' is selected from O, NH, NR ($R=C_1-C_6$ alkyl group or $R_F$);

$R_3$ is selected from a hydrogen, $C_1-C_{12}$ alkyl group, or halogen;

$R_{L3}$ is $CR_4$, N or a trivalent group, wherein $R_4$ is selected from a hydrogen, $C_1-C_{12}$ alkyl group, or halogen;

$R_F$ is —H or a functional group;

$R_x$ is a crosslinking group capable of inter- or intra-molecular crosslinking or an inter- or intra-molecularly crosslinked group; and r is an integer from about 10 to about 1000.

In certain preferred embodiments, $R_3$ is methyl.

In certain preferred embodiments, $R_{L3}$ is CH.

The trivalent group may be any suitable group. A trivalent group may include a linear or cyclic portion, serving as a spacer or linker, leading to the trivalent branching point. The branching may be at a single atom or may be at different atoms, for example, three branches from a cyclic or a linear scaffold.

$R_F$ can be any suitable functional groups, for example, $R_F$ is selected from the group consisting of amines, carboxylates, hydroxyl, halides, acyl halides, esters, azides, nitriles, amides, epoxides, aldehydes, furans, alkenes and alkynes.

In certain preferred embodiments, $R_F$ is an amine.

In certain preferred embodiments, $R_F$ is an activated carboxylic ester.

$R_x$ can be any crosslinking group group, for examples, selected from coumarin, alkenes, thiols, reactive disulfides, alkynes, furans, aldehydes and epoxides. In certain embodiments, $R_x$ may be selected to be suitable for and provide chemical reactivities, for example, to incorporate functional diversity.

r can be an integer from about 10 to about 1000 (e.g., from about 10 to about 800, from about 10 to about 500, from about 10 to about 300, from about 10 to about 100, from about 10 to about 50, from about 50 to about 800, from about 100 to about 800, from about 200 to about 800).

Unique features of the functionalizable homopolymer-based nanoparticles include a rapid synthesis method affording targeted amphiphilic polymer within 2 to 3 steps from monomer. The functional polymers can be facilely achieved because the fidelity of thiolactone chemistry makes it possible to introduce various functionalities to the polymer by reacting with amino containing functional molecules. It is also worth noting that the chemistry also provides an avenue to incorporate a secondary functionality simultaneously based on thiol chemistry.

Synthesis of Amphiphilic Homopolymer

Figure 8:
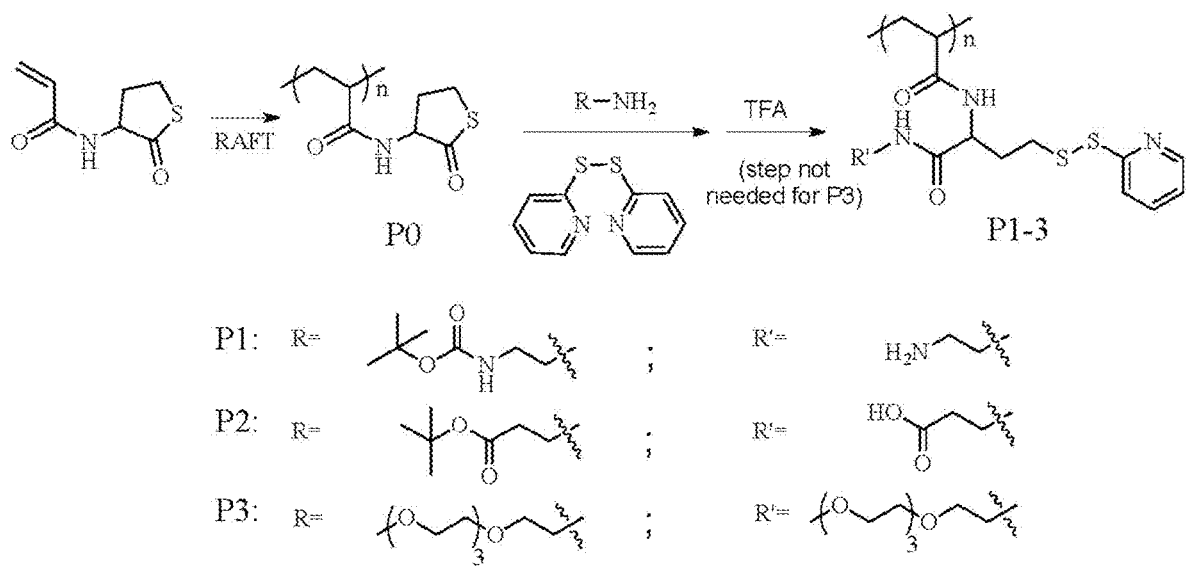
FIG. 8. Synthesis of amphiphilic homopolymer

The amphiphilic homopolymer was achieved by post-polymerization functionalization, shown in FIG. 8. Briefly, N-acryloyl homocysteine-based thialactone polymer (P0), which was prepared from RAFT polymerization was used as precursor. Amine bearing a protected functional group was used to react with the precursor opening lactone ring and generating thiol, which was captured by the aldithiol in situ affording cross-linkable disulfide. The targeted polymer (P1-3) was achieved followed by TFA deprotection if required.

Examples of amphiphilic homopolymers include:
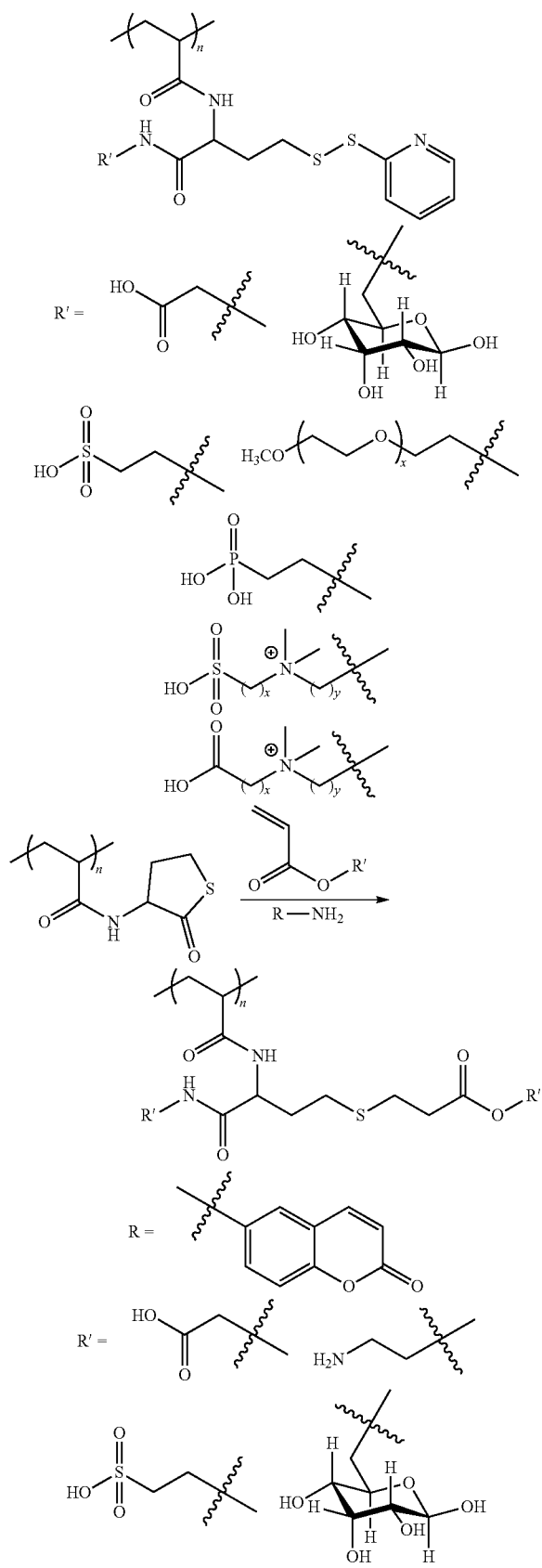
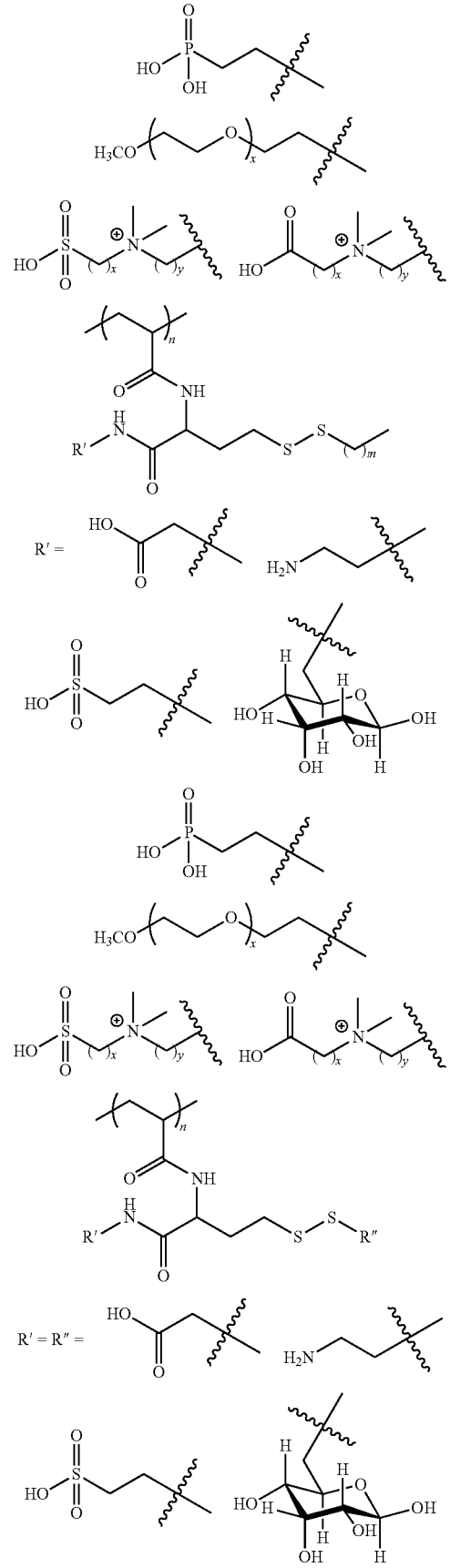

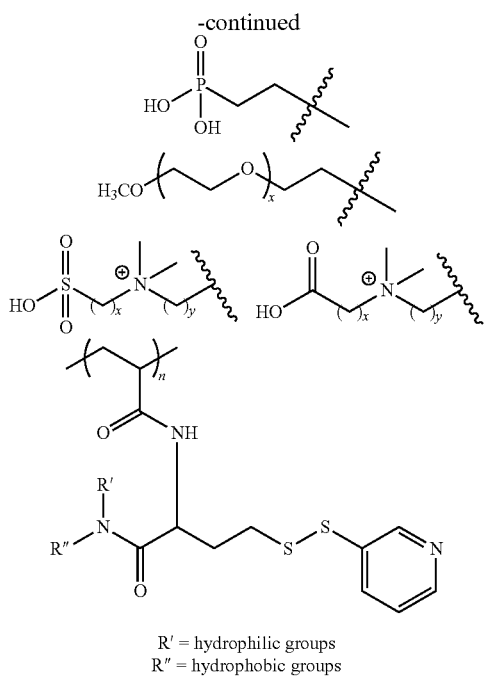

R' = hydrophilic groups
R'' = hydrophobic groups

Figure 9:
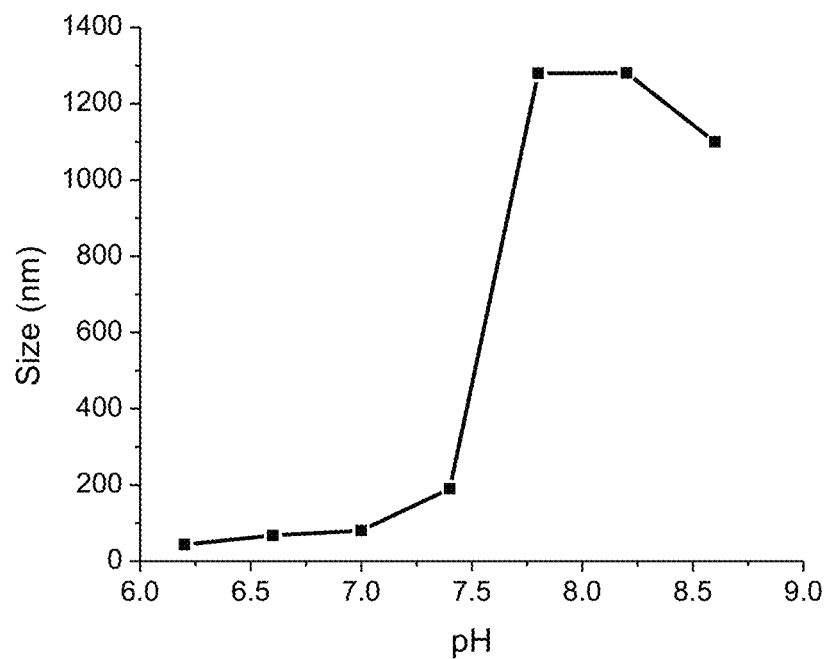
FIG. 9. Size of nanoassembly of amphiphilic homopolymer P1 (left) and P2 (right) in a variety of pHs FIG. 10. Size of nanoassembly of P1 (left) in phosphate solution and P2 in CaCl2 solution FIG. 11. Size of nanoassembly of P1 (left) in the presence of divalent anions and P2 in the presence of divalent cations.
Figure 9:
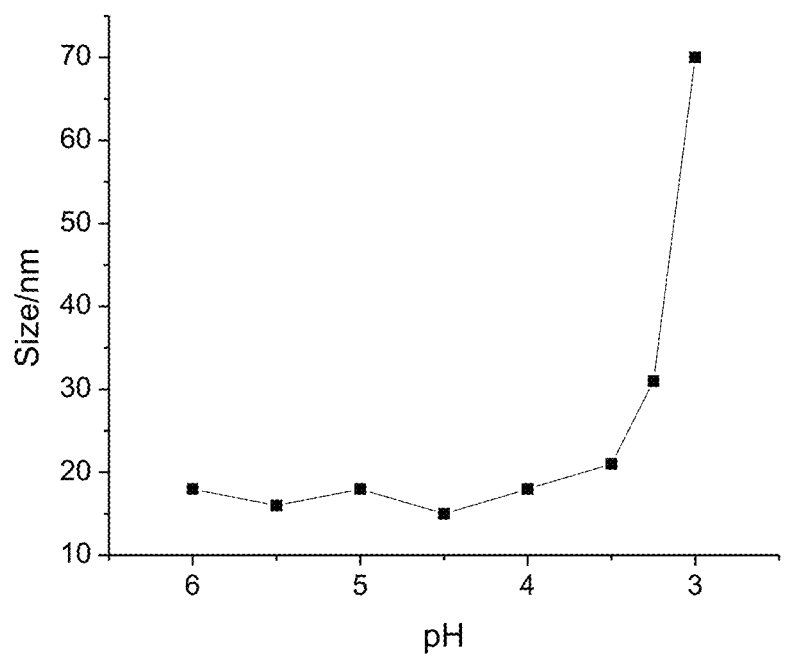

Self-Assembly of Amphiphilic Homopolymer
1. Tune the Size of Nanoassembly of Ionic Amphiphilic Homopolymer (P1, P2)
Tuning the Size by Changing pH:

The driving force for the solution assembly of amphiphilic polymer is hydrophilic lipophilic balance (HLB), which offers an opportunity for us to manipulate the self-assembly of polymer. The polymer precursors have carboxylic acid or amine functionalities which are involved in protonation-deprotonation equilibrium. By varying the pH of polymer solution, the extent to which the functionalities are ionized can be tuned to shift the hydrophilic lipophilic balance. As a result of changing in HLB, the polymer forms nano-assembly with different sizes in aqueous solution (FIG. 9).

Figure 10:
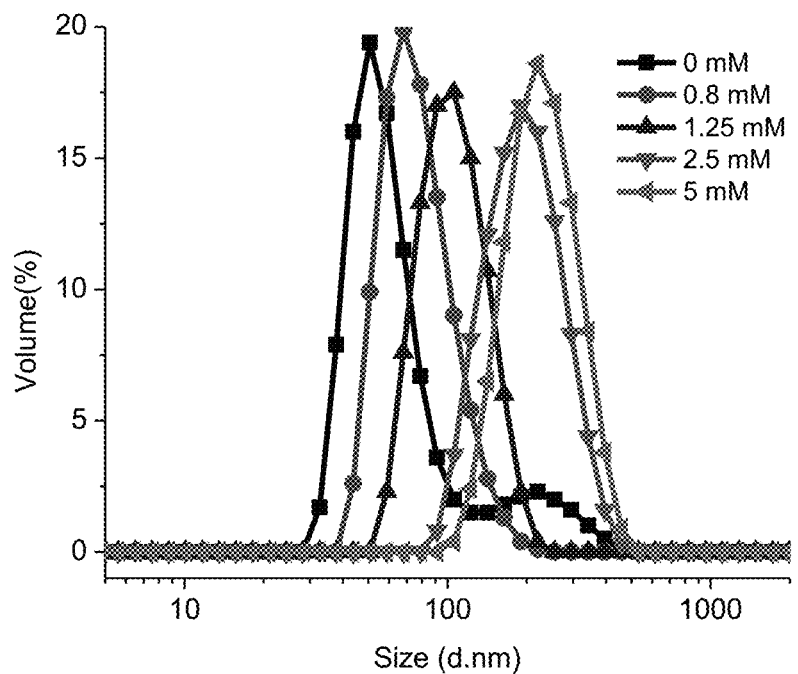
Figure 10:
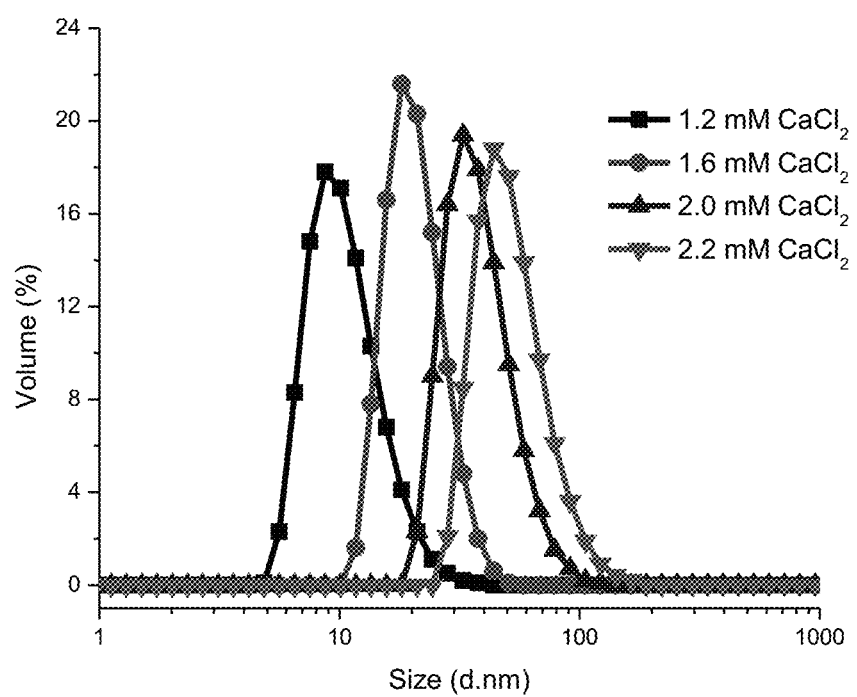

Tuning the Size by the Addition of Multivalent Counter Ion:

An alternate way to change the hydrophilicity of ammonium or carboxylate functionalities involves interaction with counter ions. A complementary divalent or trivalent counter ion was employed to polymer solution to form intra-particle salt bridges transiently crosslinking the polymer assembly. Various concentrations of counter ions were added to tune the degree of crosslinking density to tune the size of nanoparticles (FIG. 10).

Figure 11:
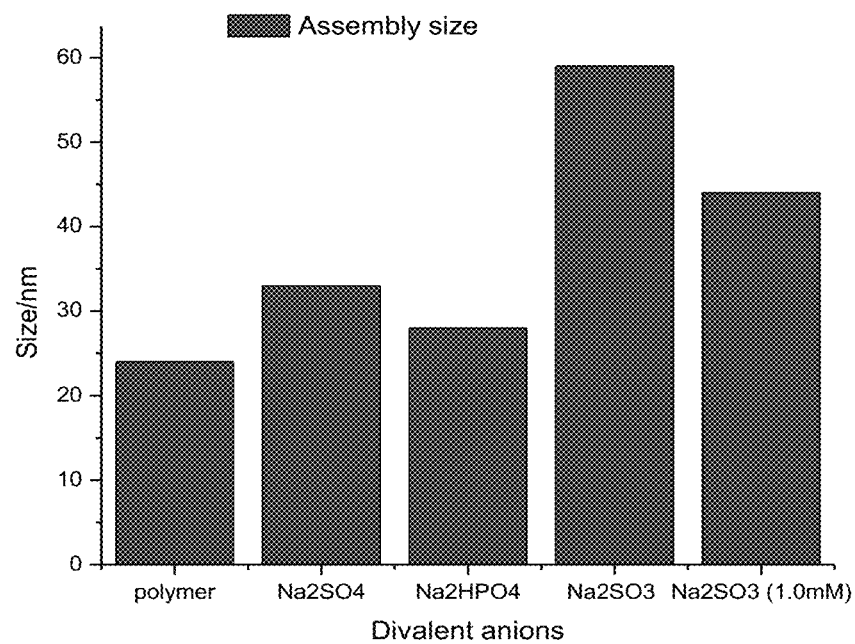
Figure 11:
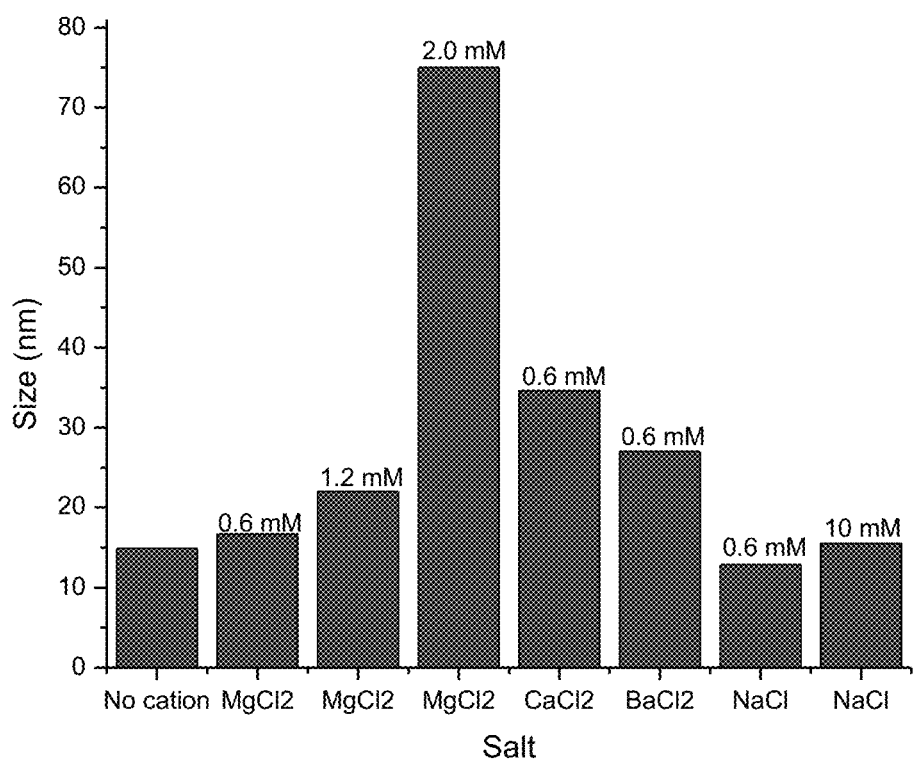

Tuning the Size by the Addition of Different Type of Counter Ions:

The binding affinity of counter ion pairs is quite different from each other, which suggests that the type of counter ions can regulate the self-assembly of polymer to different extent. A series of counter ions are shown that can tune the size of polymer nano-assembly in FIG. 11.

Figure 12:
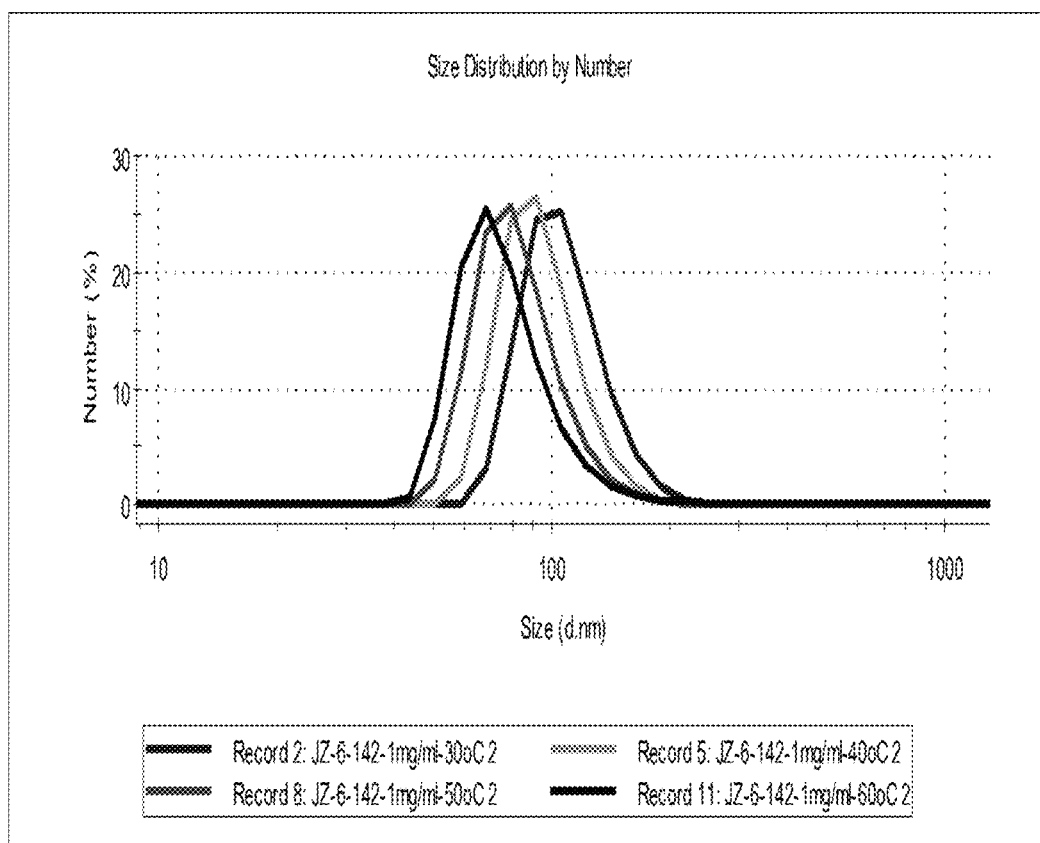
FIG. 12. Size of nanoassembly of P3 in different temperature (left) and in sodium carbonate solution (right).
Figure 12:
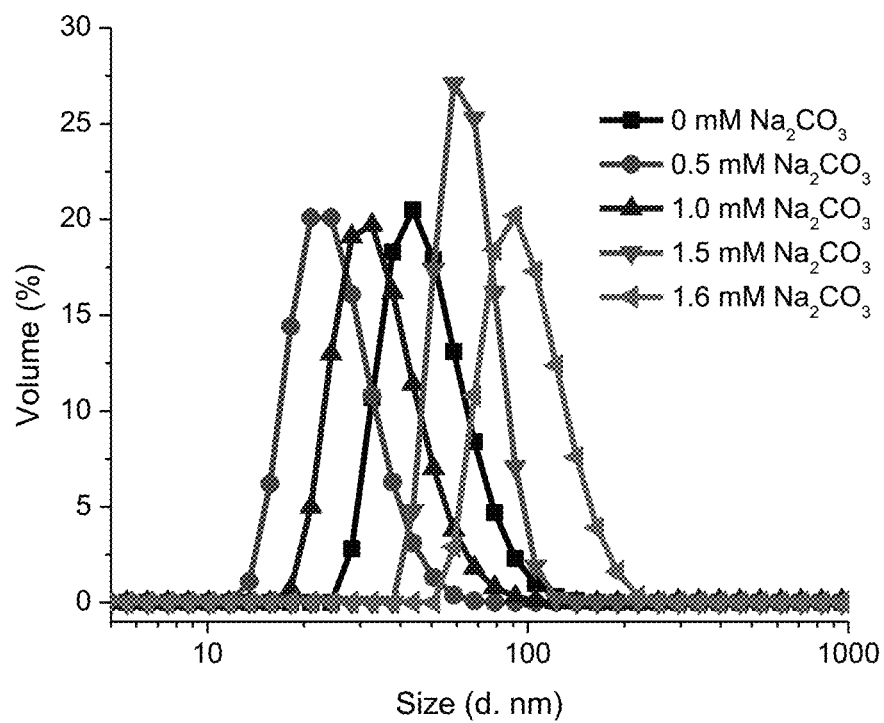

2. Tune the Size of Nanoassembly of Neutral Amphiphilic Homopolymer (P3):
Tuning the Size by Changing Temperature:

Oligoethylene glycol containing polymers are well known for their LCST behaviors. It is no surprise that oligoethylene glycol containing neurtal amphiphilic homopolymers also have LCST behavior. However, the LCST behavior can be utilized to control the size of the nanoassembly (FIG. 12).

Tuning the Size by the Addition of Salt:

A series of salt have Hofmeister effect on oligoethylene glycol containing polymer have been demonstrated. Here, salt was used to manipulate the assembly of the amphiphilic homopolymer. The size of the nanoassembly was found to increase when salt concentration is increased (FIG. 12).

Figure 13:
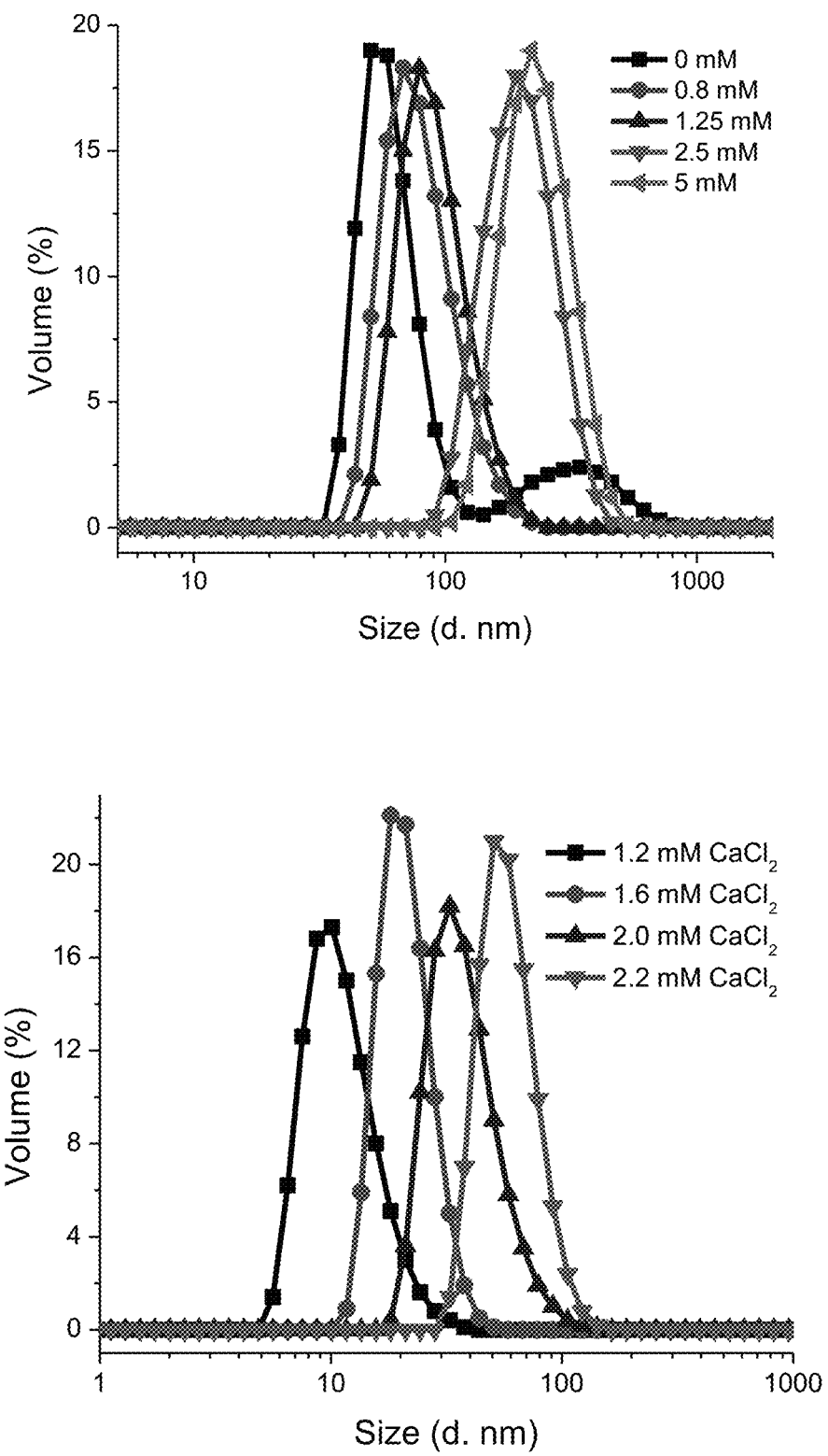
FIG. 13. Size of cross-linked nanoassembly of P1 (top), P2 (middle) and P3 (bottom).
Figure 13:
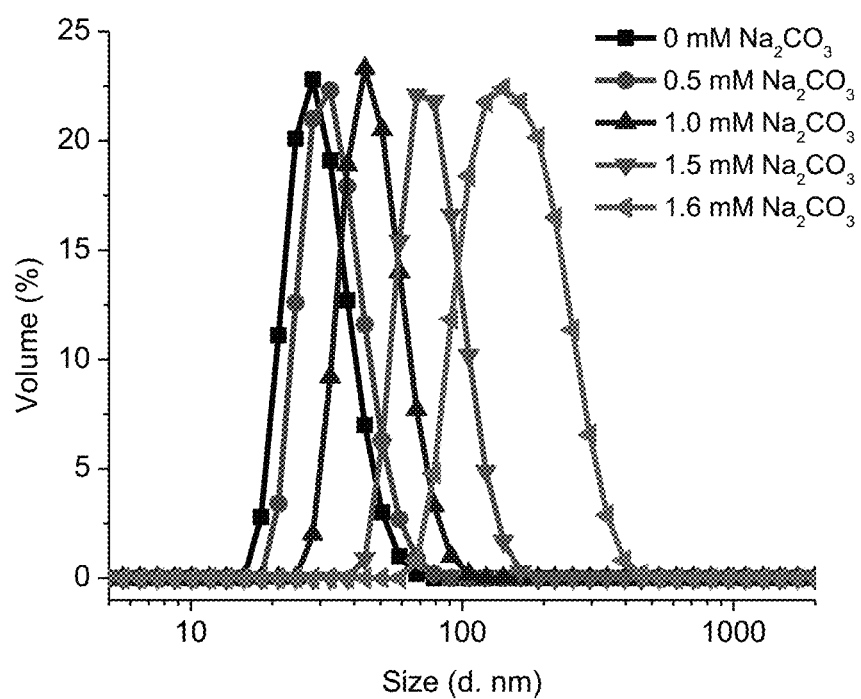

Cross-Linked Nanoassembly of Amphiphilic Homopolymer Nanoassembly:

Regarding the application of nano-assembly, structural and morphological stability of the assembly are highly desired. In order to stabilize the nano-assembly, chemical cross-linking was used to covalently stabilize the nano-assembly via the addition of DTT. The addition of DTT results in the formation of disulfide bond inside the nano-assembly locking the nano-assembly. The approach applied to regulate the self-assembly of amphiphilic homopolymer can be translated to prepare the cross-linked particles. By varying pH, salt concentration, salt species and polymer solution temperature, the size of cross-linked nano-assembly can be controlled in a wide range (FIG. 13).

Post-Functionalization:

The performance of nanoparticles for biomedical application is highly dependent on their surface properties. The ability to functionalize the hydrophilic corona of polymersome allows one to optimize its performance and also expand the polymersome inventory for other potential applications. Pegylation of both cationic and anionic VesiGels were used to demonstrate the surface functionalization of hydrphoilic corona. NHS ester and amine terminated polyethylene glycol monomethyl ether were used to treat amino and carboxylate-containing VesiGel respectively. The successful peglation of the two types of VesiGels was confirmed by following their surface charges before and after the functionalization.

Figure 18:
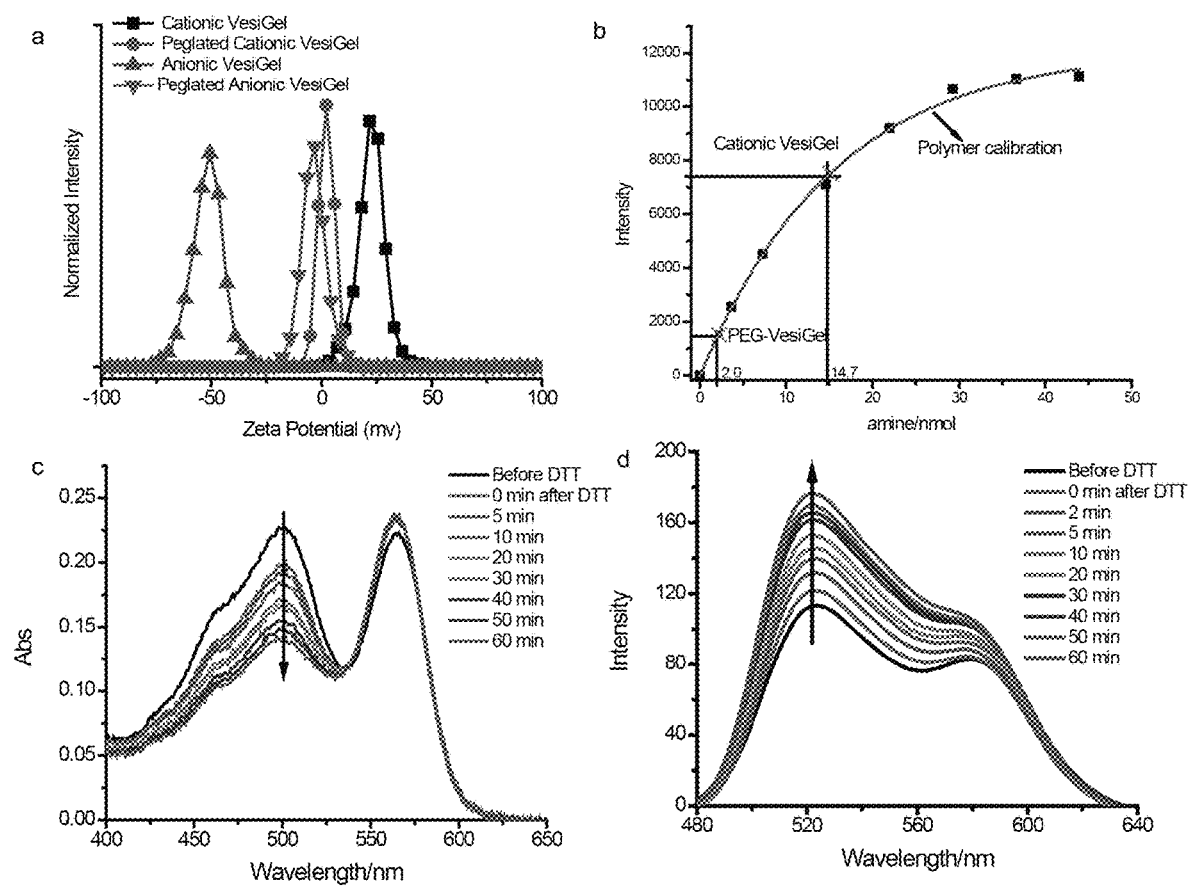
FIG. 18. (a) Changes on the surface charge of VesiGels upon peglation; (b) measurement of functionalizable amine by fluorescamine assay; (c) absorbance evolution of FRET pair functionalized VesiGel upon DTT treatment; (d) emission evolution of FRET pair functionalized VesiGel upon DTT treatment.

As shown in FIG. 18a, a neutral zeta potential was observed after the pegylation from both original cationic or anionic VesiGel. The degree of functionalization of cationic VesiGel was measured by fluorescamine assay as shown in FIG. 18b. 14.7 nmol out of 36.6 nmol of amine groups on cationic VesiGels can be accessed for fluorescamine functionalization indicating 40% of functionalizable amine groups. 86% of this 40% (2.0 nmol out of 14.7 nmol can not be accessed) of functionalizable amines on VesiGel can be pegylated. The lack of full pegylation when compared to fluorescamine is likely because of the limited accessibility of PEG (Mn: 2000 Da) to amines.

It is desirable to control over the permeability of polymersomes to tune the mass transportation between media and polymersome lumen for the applications like nanoreactor or artificial organelles where the disruption of the vesicular structure is not desired. A potential solution to manipulate the transportation process can be tuning the hydrophobicity of vesicle wall by post-functionalization. This can also be an effective way to covalently incorporate the active components into the nanoassembly for therapeutic delivery applications. Independent functionalization of the hydrophilic corona and hydrophobic wall of the VesiGel would help demonstrate the versatility of the VesiGel platform for post-functionalization.

Taking the advantage of amino group and the left over pyridinyl disulfide, the VesiGel can be orthogonally functionalized with a FRET pair by reacting with the complementary isocynate containing rhodamine and thiol bearing fluorescein. The functionalization permanently immobilized rhodamine onto the corona with a thiourea linkage, but fluorescein onto hydrophobic wall with a cleavable disulfide bond. Concurrent observation of the absorbance of both dyes and FRET after extreme dialysis suggests the success of the functionalization (FIGS. 18c and 18d).

To further test the difference on the reversibility of the two chemistries applied for functionalization, the VesiGel was treated with DTT which selectively cleave fluorescein from the nanoparticle. It was envisioned that the cleavage of fluorescein will result in precipitation out from solution, therefore, the decrease of absorbance while the absorbance of rhodamine remains the same because it still attached. This was indeed observed. The increase in the emission of fluorescein after the addition of DTT also indicated the cleavage of fluorescein. The increasing fluorescence can be attributed to the disappearance of FRET due to the lack of proximity between rhodamine and fluorescein molecules. Another possible reason for the fluorescence recovery of fluorescein can be due to the decrease in self-quenching of fluorescein after cleavage from VesiGel. All these observations suggest orthogonal functionalization of hydrophilic corona and hydrophobic wall can be done on the disclosed VesiGel.

Guest Loading and Stimuli-Triggered Release

Figure 14:
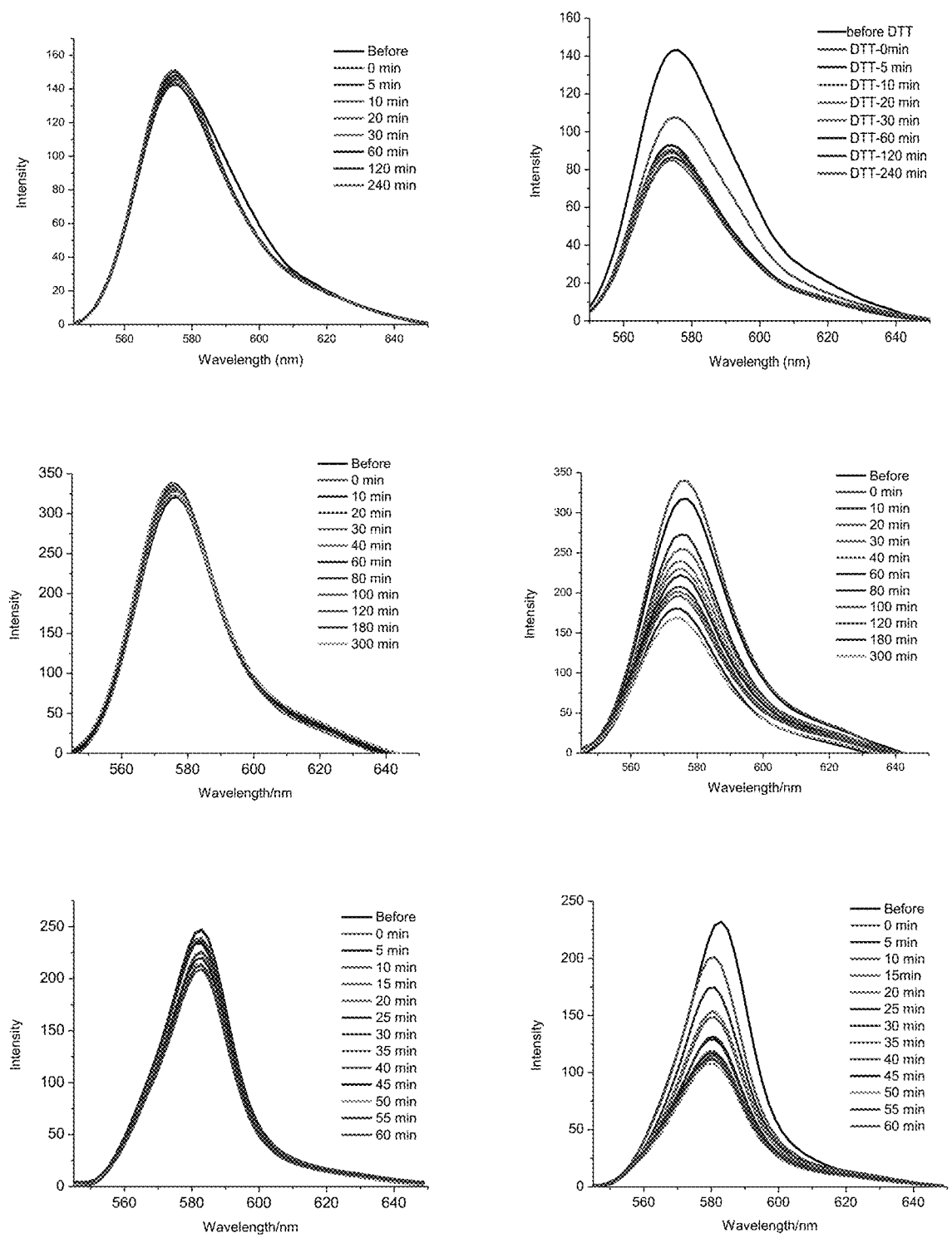
FIG. 14. Reductant triggered guest release from cross-linked nano-assembly prepared from P1 (top), P2 (middle) and P3 (bottom). Left panel: control w/o reductant; Right panel: w/reductant.

The amphiphilicity of polymer allows the nano-assembly to encapsulate guest molecules. Due to the disulfide functionality in the nano-assembly, it should have responsiveness toward applied trigger, reductant, which reduces the disulfide bond and destabilizes the nano-assembly causing the release of loaded guest molecules. The ross-linked nano-assemblies are indeed found to release the loaded guest molecule when a redundant was added into nano-assembly solution (FIG. 14).

Figure 19:
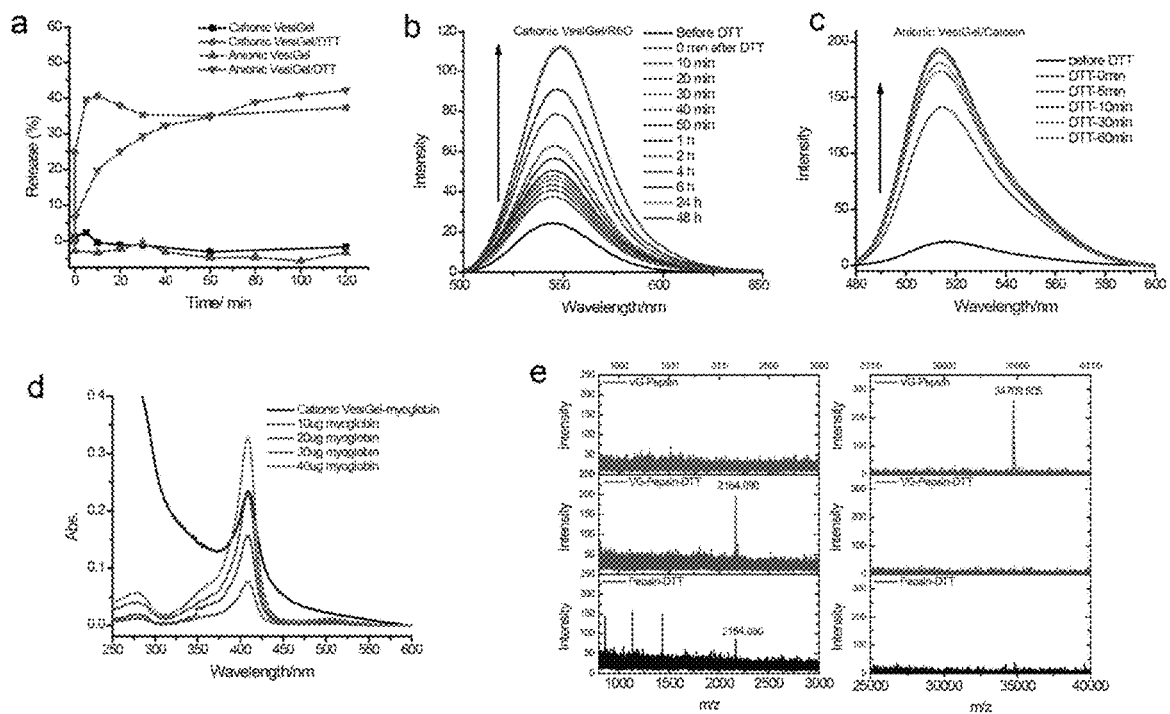
FIG. 19. (a) Hydrophobic guest released triggered by DTT; (b) R6G released from cationic VesiGel; (c) Calcein released from anionic VesiGel; (d) Encapsulation of Myoglobin in cationic VesiGel followed by Uv-vis; (e) Lysozyme released from anionic VesiGel followed by MALDI after trypsin digestion.
Figure 20:
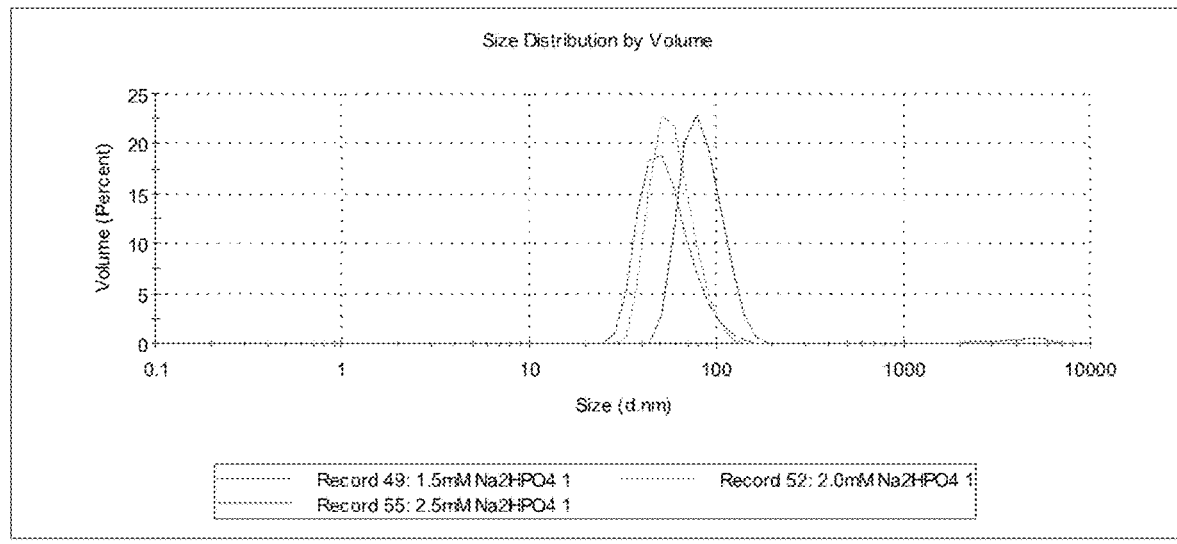
FIG. 20. DLS of P1 in $Na_2HPO_4$ solution with different concentrations before crosslinking.
Figure 21:
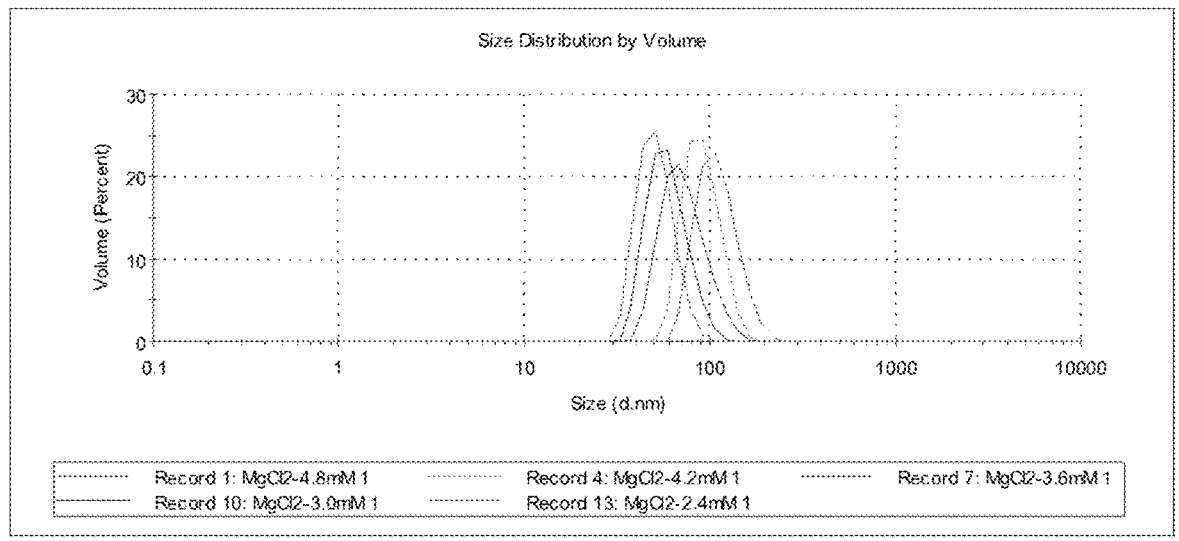
FIG. 21. DLS of P2 in $MgCl_2$ solution with different concentrations before crosslinking.
Figure 22:
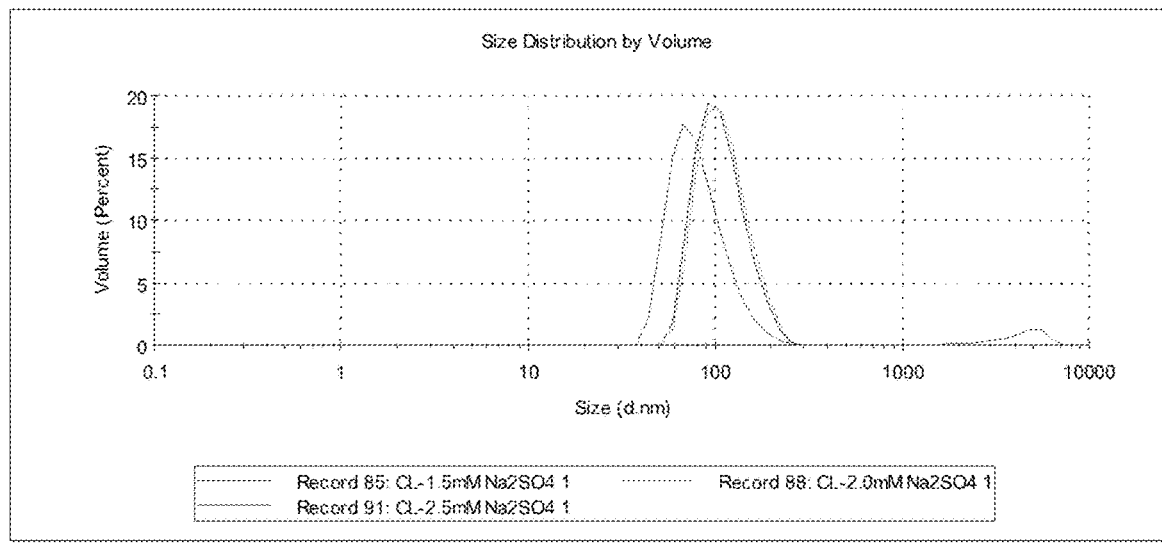
FIG. 22. Salt concentration dependant nanoassembly size of P1 in a variety of salt after crosslinking.
Figure 23:
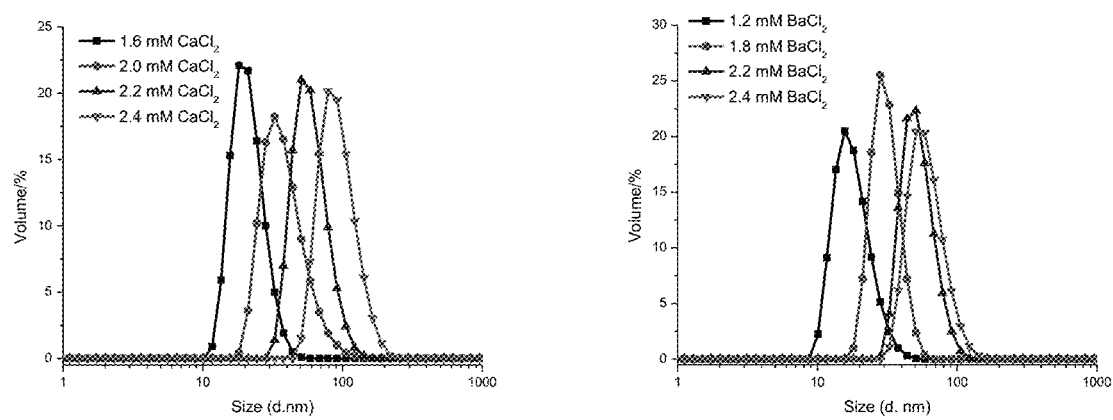
FIG. 23. Salt concentration dependant nanoassembly size of P2 in $CaCl_2$) and $BaCl_2$ after crosslinking.
Figure 24:
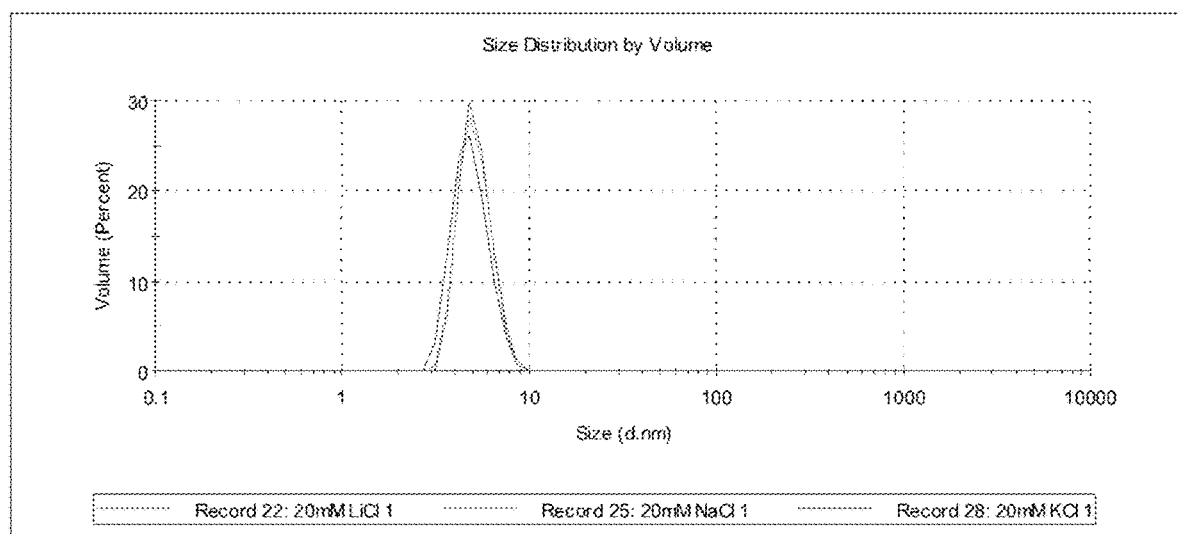
FIG. 24. Size of P1 in 10 mM slat solution with different cations (Top) and P2 in 20 mM salt solution with different anions (bottom).
Figure 25:
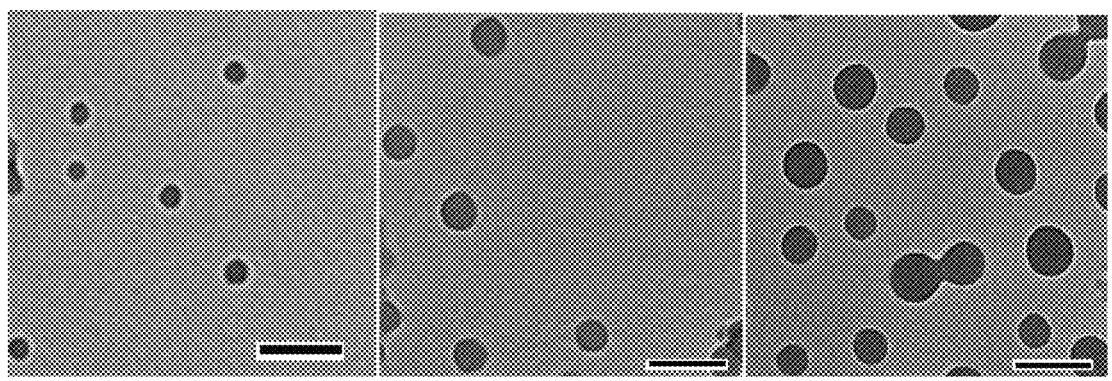
FIG. 25. TEM image of cationic VesiGel prepared in 1.5 mM (left), 2.0 mM (middle), and 2.5 mM (right) $Na_2HPO_4$. The scale bar is 100 nm.
Figure 26:
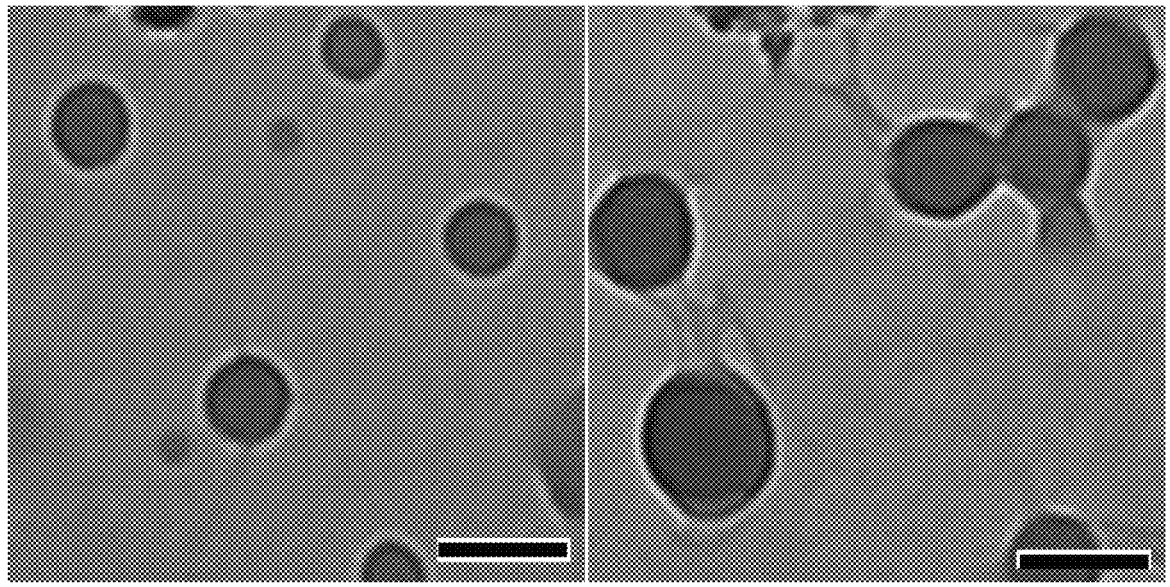
FIG. 26. TEM image of cationic VesiGel prepared in 1.5 Mm (left), 2.0 mM (right) $Na_2SO_4$ solution. The scale bar is 100 nm.
Figure 27:
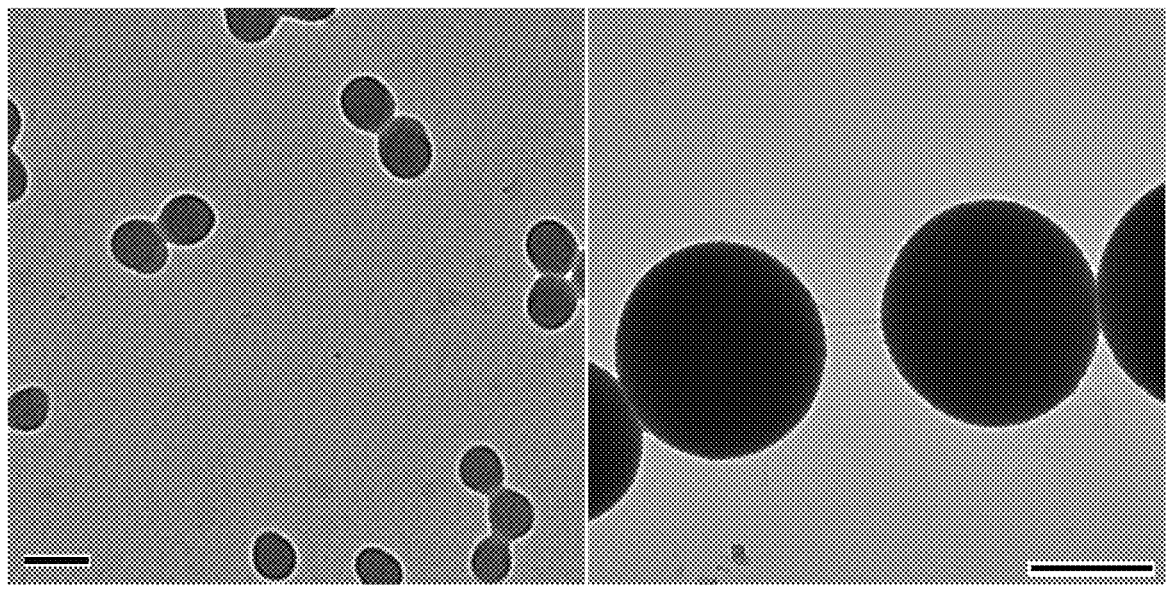
FIG. 27. TEM image of cationic VesiGel prepared in 1.25 mM (left, scale bar: 100 nm) and 1.5 mM (right, scale bar: 500 nm) $Na_2SO_3$ solution.
Figure 29:
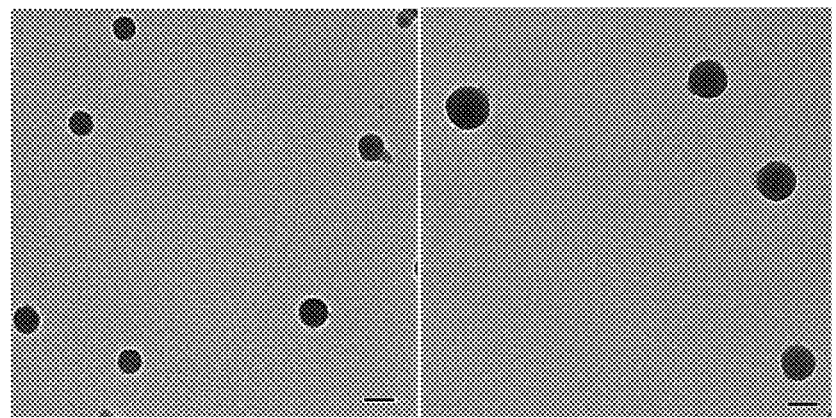
FIG. 29. TEM image of anionic VesiGel prepared in 2.4 mM (top left), 3.0 mM (top middle), 3.6 mM (top right), 4.2 mM (bottom left) and 4.8 mM (bottom right) $MgCl_2$ solution. The sacle bar is 100 nm.
Figure 30:
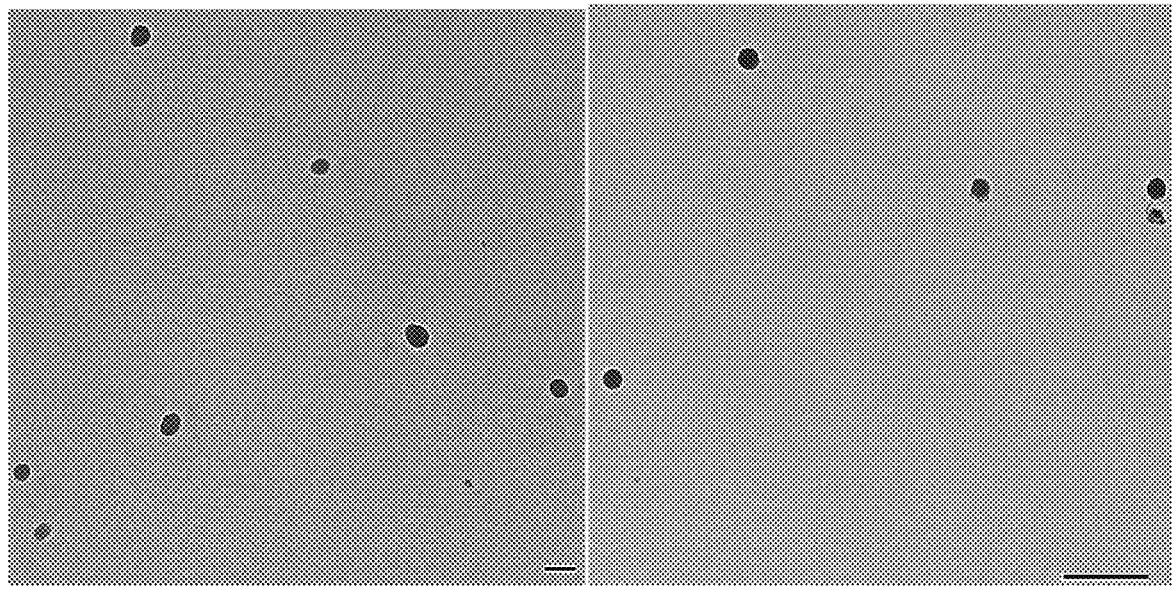
FIG. 30. TEM image of anionic VesiGel prepared in 2.4 mM $BaCl_2$ (left, scale bar: 100 nm) and 2.2 mM $CaCl_2$ (right, scale bar: 500 nm) $MgCl_2$ solution.

The unique structural features having hydrophobic wall and hydrophilic lumen simultaneously, gives the polymersome the capability of serving as a reservoir for both hydrophobic and hydrophilic cargos. Bearing this structural characteristic along with the disulfide crosslinks, the disclosed VesiGels are expected to be able to encapsulate hydrophilic and hydrophobic cargos and have features of redox-triggered cargo release. Initially, DiI, a hydrophobic dye was encapsulated in VesiGels. The release of DiI was observed in the presence of DTT, which disrupts the VesiGel by breaking the disulfide crosslinks (FIG. 19a). In contrast, no observation of encapsulated DiI was found without external stimuli.

To test the ability to load the hydrophilic cargos, cationic and anionic VesiGels was formed in rodamine 6G and calcein solution respectively, where the hydrophilic cargos were expected to be engulfed into the cavity of polymersome in situ. So, even after the extensive dialysis, the local concentration of dye in VesiGel lumen is the same as that of the original dye solution which is high enough for self-quenching. Fluorescence recovery from both cationic and anionic VesiGels was observed upon the treatment of DTT (FIGS. 19b and 19c). The reason for the observation of fluorescence recovery is that disruption of vesicular structure by DTT reduction liberates dye molecules from VesiGel lumen into bulk solution. As a result of release from VesiGel, the dye concentration is diluted to be lower than the concentration that is required for self-quenching. Therefore, an increase in fluorescence can be observed in response to the treatment of DTT.

Formulating the biomacromolecules into nanostructure for therapeutic or catalysis application is of much more interest. Here, myoglobin (Mw: 17 kDa, pI: 7.2) was chosen as a model protein to load into cationic VesiGels following the same procedure of rhodamine 6G encapsulation. As shown in FIG. 19d, the loading of myoglobin after removal of free myoglobin was followed by measuring the absorbance of myoglobin at 408 nm attributed to the porphyrin absorption. By fitting in the calibration curve generating by pure myoglobin solution, 3 wt % of myoglobin can be encapsulated in the VesiGel. Pepsin (Mw: 35 kDa, pI 4.2) was also encapsulated in to anionic VesiGels using the same protocol. While not exclusive, positively charged proteins are encapsulated more efficiently in positively charged vesigels and negatively charged proteins with negatively charged vesigels. This is an unusual combination.

The success of encapsulation was evident by the observation of tyrosine absorption and emission. The release of pepsin triggered by the DTT was demonstrated by trypsin digestion assay detected by mass spectrometry. The basic design on this assay is that pepsin is prevented from being digested when it is trapped inside an intact VesiGel, while the disruption of VesiGel by DTT makes the pepsin accessible for digestion.

In FIG. 19e, signal with an m/z of 34709.605 that originates from pepsin was observed from pepsin encapsulated in VesiGel without DTT exposure after trypsin digestion. However, the corresponding signal was not observed from pepsin itself or pepsin encapsulated in VesiGel followed by DTT treatment after trypsin digestion indicating the consumption of pepsin by trypsin digestion. All of these evidences together suggest the release of pepsin from VesiGel can be obtained by applying DTT to VesiGels.

Thus, the invention discloses a general methodology for the preparation of size-tunable VesiGel platform directly from synthetically easily accessible homopolymers aqueous solution in the assistance of multivalent counter ions via salt-bridging mechanism. This method provides a variety of physical and chemical properties including: i) variable surface functionalities: ii) capability of simultaneous encapsulation of hydrophilics and hydrophobics; iii) engineerable corona and membrane; iv) redox-modulated programmable host-guest property into a single VesiGel system. The simplicity and versatility of this method to prepare VesiGel with engineerable properties will profoundly facilitate and extend the applications of the vesicular nanostructures.

Functional VesiGels

Figure 15:
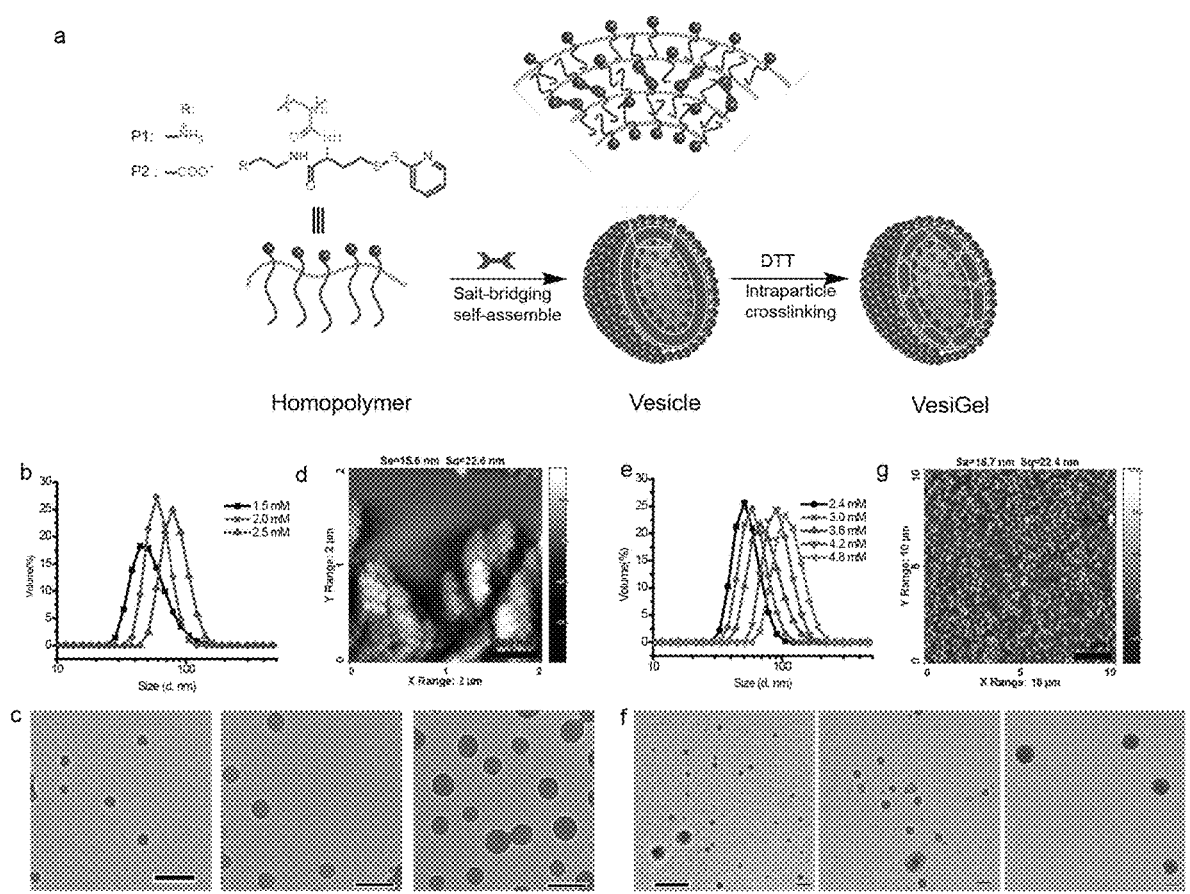
FIG. 15. (a) Schematic presentation of slat-induced formation of polymersome; (b) $Na_2HPO_4$ concentration dependent sizes of polymersomes prepared from P1; (c) TEM images of polymersomes prepared in $Na_2HPO_4$ (left: 1.5 mM; middle: 2.0 mM; right: 2.5 mM); (d) AFM image of polymersome prepared from P1 in 2.5 mM $Na_2HPO_4$; (e) $MgCl_2$ concentration dependent sizes of polymersomes from P2; (f) TEM images of polymersomes prepared in $MgCl_2$ (left: 2.4 mM; middle: 3.6 mM; right: 4.8 mM); (g) AFM image of polymersome prepared from P2 in 4.2 mM $MgCl_2$.

As disclosed herein, instead of using copolymers with complex architectures, typically block copolymers, simple homopolymers are used as polymersome precursor synthetically saving tremendous efforts on polymer preparation. The targeted polymers are amphiphilic homopolymers comprised of a hydrophilic head group (amino or carboxylate) and a hydrophobic and cross-linkable group (pyrdinyl disulfide), as shown in FIG. 15a.

Thus, the approach takes advantage of the fidelity of the thiolatone ring opening reaction to prepare amphiphilic homopolymer. (Reinicke, et al. 2013 *ACS Macro Lett.* 2, 539-543; Espeel, et al. 2012 *Polym. Chem.* 3, 1007-1015.) The ring opening reaction of poly(thiolactone acrylamide) (PT1a) homopolymer was initiated by N-Boc ethylenediamine or β-alanine t-butyl ester generating an amide and thiol which was captured by excessive amount of aldrithiol in situ. Removal of protecting group by TFA gives the targeted amphiphilic homopolymers bearing ionic head groups and crosslinkable hydrophobic disulfide tails.

Single tailed small molecule surfactants with opposite charges that normally form micelles have been mixed at appropriate ratio to construct so-called "catanionic" vesicles. (Segota, et al. 2006 *Adv. Colloid Interface Sci.* 121, 51-75; Iampietro, et al. 1998 *J. Phys. Chem. B.* 102, 3105-3113.) Besides, multivalent counter ions have also been employed to induce the formation of vesicular structures. (Lee, et al. 2013 *Soft Mater* 9, 200-207; Li, et al. 2014 *Adv.*

*Funct. Mater.* DOI: 10.1002/ADFM.201400569.) The formation of vesicular structure is attributed to the reduction in the area of hydrophilic head group due to the counter ion pairing changing the molecular packing parameters.

The herein disclosed approach takes advantage of the interaction between polyions and their counter ions to modulate the self-assemble process. The addition of divalent counterions adjusts the hydrophilic lipophilic balance of the homopolymer, along with the molecular packing parameters, to adopt the vesicular type assembly. The cationic homopolymer, P1 was found to form polymersomes in $Na_2HPO_4$ solution with a low millimolar salt concentration. The size of polymersomes readily increases from 40 nm to 90 nm when the concentration of $Na_2HPO_4$ increases from 1.5 mM to 2.5 mM (shown in SP).

The assembled polymersome can be further covalently stabilized by intraparticle disulfide crosslinking to lock the vesicular morphology. The size of VesiGel, shown in FIG. 15b, retains almost the same after the crosslinking suggesting the intra-particular crosslinking occurs. The TEM images indicate the nanoassemblies of P1 adopt vesicular structures in all investigated $Na_2HPO_4$ concentrations. Size of the VesiGel measured by DLS is coincident with that determined by TEM and AFM.

Similarly, when anionic polymer, P2 was used as a precursor, $MgCl_2$ can be used to induce the formation of anionic polymersome, which was confirmed by TEM. The size of obtained anionic polymersome was also found to be $MgCl_2$ concentration dependant. Tunable size ranging from 45 nm to 120 nm was obtained when concentration of $MgCl_2$ was increased from 2.4 mM to 4.8 mM. The crosslinking of anionic polymersome was also intra-particular indicated by the observation of similar particle size after and before crosslinking.

To further confirm VesiGels do have vesicular structure, radius of gyration ($R_g$) of the VesiGels prepared in 2.4 mM and 4.8 mM $MgCl_2$ solution were by SLS to compare with their hydrodynamic radius ($R_h$) obtained from DLS. It turns out that $R_g/R_h$ of VesiGels prepared in 2.4 mM and 4.8 mM is respectively measured to 1.19 and 0.99. The measured $R_g/R_h$ values are closed to 1.0, which is the theoretical value for a vesicle. (Benoit, H., Froehlich, Light scattering from polymer solutions, edited by Huglin, M. B. (Academic Press, London, 1972).) A larger $R_g/R_h$ value for small VesiGels prepared in 2.4 mM $MgCl_2$ solution indicates a loose vesicular structure that was also confirmed by the blurred structure from TEM image.

Figure 16:
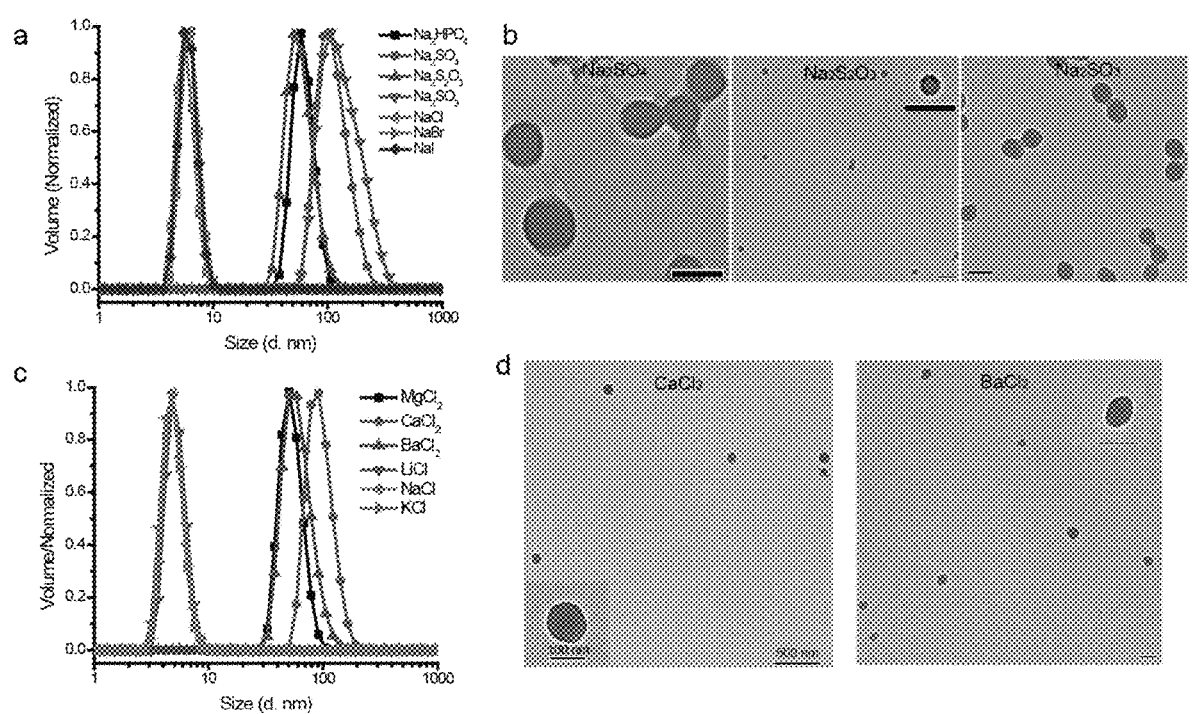
FIG. 16. (a) Sizes of P1 in different salts; (b) TEM image of cationic VesiGel; (c) sizes of P2 in different salts; (d) TEM image of anionic VesiGel. Scale bars are 100 nm, unless noted.

To test if salt-induced formation of the polymersome can be generally applied, a variety of salts were employed to polymer solution followed by the measurement of the size of the nanoassembly. The size of nanoassembly from P1 in the presence of $Na_2SO_4$, $Na_2S_2O_3$, and $Na_2SO_3$ was found to be significantly affected by the salt species (FIG. 16a). The morphology of nanoassemblies obtained from these salts was also found to be vesicular from TEM (FIG. 16b). Similar to $MgCl_2$, the influence of $CaCl_2$ and $BaCl_2$ on self-assembly of P2 was also observed and vesicular structure was adopted in both cases evident by the TEM. Importantly, the size of nanoassemblies of P1 and P2 in these salts solutions all increase with increasing salt concentration.

In addition to these divalent salts, the effect of monovalent salts on self-assembly of both polymers was also investigated. Nanostructures around 6 nm were obtained in the presence of monovalent salts. These nanostructures with much smaller size are likely single chain nanoparticles due to the polymer chain collapse after cross-linking. It is worth noting that the concentration of monovalent salts used in both case are much higher than that of divalent salts (4-5 times). It is clear that the salts having divalent counter ions to corresponding polymers remarkably affect their self-assembly. Along with the lack of influence of monovalent salts on polymer assembly, the observation of divalent counterions mediated self-assembly suggests that operating mechanism of polymersome formation assisted by these salts can potentially be through salt-bridging.

Mechanistic Study on VesiGels Formation

It was proposed that the divalent counter ion interacts with two hydrophilic head groups of the polymer reducing the hydrophilicity of the polymer, consequently adjusting the packing parameters to meet the requirement for polymersome formation. On the other hand, salt-bridging also stabilize the lamellar packing of polymer chains on the vesicle wall. This hypothesis is also supported by the observation of salt-bridging induced morphological transformation of block copolymer assemblies from micelle to vesicle. (Zhang, et al. 1996 *Science*, 272, 1777-1779; Zhang, et al. 1996 *Macromolecules* 29, 8805-8815.) However, the proposed salt-bridging mechanism was not yet systematically investigated.

To test this theory, the polyions were mixed with a water-soluble dye, as a substitute of salt, which has multivalent counter ions to interact with the polymer. As shown in FIG. 17a, if the interaction causes the aggregation, the probe molecules will be brought closer by the polymer leading to a red-shift on absorbance as well as fluorescence quenching. (Grohn, et al. 2008 *Chem. Eur. J.* 14, 6866-6869; Yildiz, et al. 2009 *Macromol. Chem. Phys.* 210, 1678-1690.) Probes used were calcein and lysine modified pyrene respectively for P1 and P2. As shown in FIG. 17b, observed was a clear red-shift of probes on absorbance spectrum after the addition of polymers with opposite charge. Concurrently, an obvious fluorescence quenching was also observed in both probes.

Interestingly, excimer emission was observed from dimerized pyrene due to the proximity of the probe in polymer nanoaggregate. In addition, the lack of observation of the absorbance red shifting and fluorescence quenching of probes when polyions are mixed with probes of the same charge further supported the electrostatics-based hypothesis (FIGS. 17d and 17e). Furthermore, increases of the size of polymer assembly in the presence of the probes were also found as previously observed, when divalent or trivalent salts were to induce the assembly.

Figure 17:
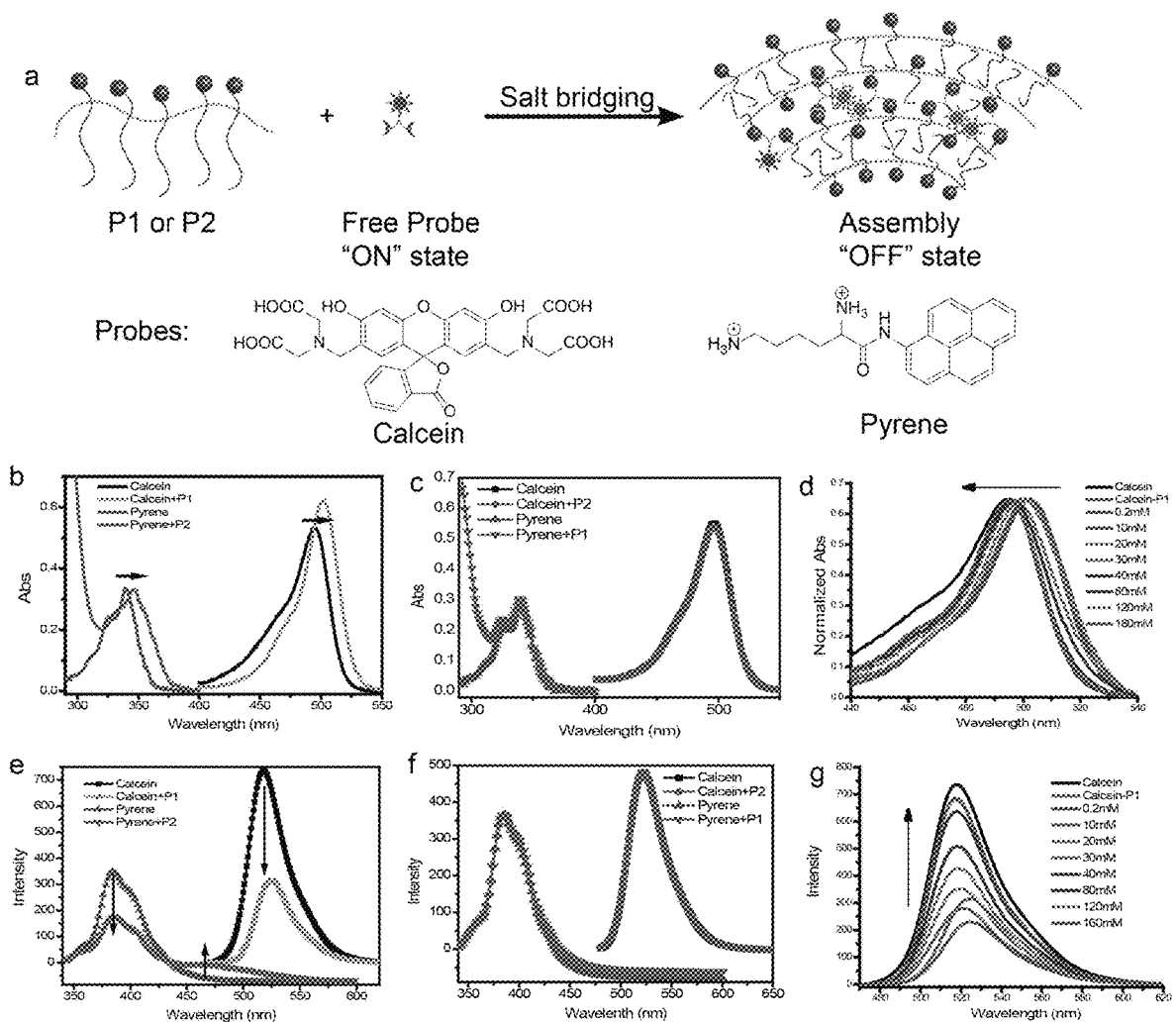
FIG. 17 (a) Schematic illustration of salt-bridging mechanism probed by fluorescent dyes; (b) UV-vis of probes mixed with polymers with opposite charge; (c) UV-vis of probes mixed with polymers with same charges; (d) spectroscopic evolution on calcein-P1 complex absorbance titrated by $Na_2SO_4$; (e) fluorescence of probes mixed with polymers with opposite charge; (f) fluorescence of probes mixed with polymers with same charges; (g) spectroscopic evolution on calcein-P1 complex emission titrated by $Na_2SO_4$.

To further test this theory, a salt competition experiment was also performed, in which change on absorbance and fluorescence of a pre-mixed P1/calcein solution was followed, when the solution was titrated by $Na_2SO_4$. Here, it was envisioned that sulfate anions act as a competetiver binder with the cationic polymer and liberating the calcein probe from polymer/calcein complex, therefore, changing the photophysical properties of the probe. As released from the complex, the maximum absorption of calcein will be gradually blue shifted to its original one when it is completely freed from the complex. This was indeed observed and the data are shown in FIG. 17. On the other hand, the self-quenching of calcein will be also eliminated due to the lack of proximity of probes in the presence of competing sulfate ions. Fluorescence recovery of calein was also clearly observed in the course of sulfate titration.

Experimental

Materials and Methods

Polymer stock solution preparation. 15 mg of P1 or P2 was directly dissolved in 2 mL of milliQ water. To make P2 dissolved, 1.5 eq. of NaOH was added to the solution. The obtained solution was then dialyzed against DI water using membrane with a MWCO of 3500 Da. The final concentration of solution was fixed to 5 mg/mL.

Polymersome and VesiGel formation. Calculated amount of salt stock solution (100 mM) was added to 300 μL of milliQ water. To the above slat solution, 200 μL of P1 stock solution was added to make final polymer solution with a concentration of 2 mg/mL. For P2, 400 μL of salt solution was prepared and added with 100 μL of P2 stock solution giving the polymer solution with a concentration of 1 mg/mL. The final polymer solutions were left for 3 hours to form polymersomes. The VesiGels were obtained by cross-linking the polymersome solution through the addition of calculated amount of DTT. The cross-linking reaction was allowed to undergo for 4 hours. The VesiGel was then purified by dialysis against water.

Guest molecules encapsulation. For hydrophobic guest encapsulation, 1 wt % of guest solution (1 mg/mL) in acetone was added to the polymersome solutions followed by the addition of DTT. The unloaded guest molecule was removed by filtration using syringe filter with a pore size of 0.4 μm. The hydrophilic guests were dissolved in the salt solution with a desired salt and guest concentration. To the solution, polymer stock solutions were added to form polymersomes which encapsulate the hydrophilic guest in situ. The free guest was removed by extensive dialysis against water after DTT crosslinking.

Polymer Stock Solution Preparation.

15 mg of P1 or P2 was directly dissolved in 2 mL of milliQ water. To make P2 dissolved, 1.5 eq. of NaOH was added to the solution. The obtained solution was then dialyzed against DI water using membrane with a MWCO of 3500 Da. The final concentration of solution was fixed to 5 mg/mL by adding milli Q water.

Polymersome and VesiGel Formation.

Calculated amount of salt stock solution (100 mM) was added to 300 uL of milliQ water. To the above salt solution, 200 μL of P1 stock solution was added to make final polymer solution with a concentration of 2 mg/mL. For P2, 400 uL of salt solution was prepared and added with 100 μL of P2 stock solution giving the polymer solution with a concentration of 1 mg/mL. The final polymer solutions were left for 3 hours to form polymersomes. The VesiGels were obtained by cross-linking the polymersome solution through the addition of calculated amount of DTT. The cross-linking reaction was allowed to take place for 4 hrs. The VesiGel was then purified by dialysis against water.

Small Guest Molecules Encapsulation.

For hydrophobic guest encapsulation, 1 wt % of guest solution (1 mg/mL) in acetone was added to the polymersome solutions followed by the addition of DTT. The unloaded guest molecule was removed by filtration using syringe filter with a pore size of 0.4 um. The hydrophilic guests were dissolved in the salt solution with a desired salt and guest concentration. To the solution, polymer stock solutions were added to form polymersomes which encapsulate the hydrophilic guest in situ. The free guest was removed by extensive dialysis against water after DTT crosslinking.

Myoglobin Encapsulation.

2 mg/mL of myoglobin was dissolved in 1 mL of milliQ water. 11 μL of $Na_2HPO_4$ solution (100 mM) was added to 289 μL of myoglobin solution. 100 μL of P1 solution was added to myoglobin-$Na_2HPO_4$ solution followed by the addition of 0.1 equivalent of DTT after 2 hrs. The free myoblobin was removed 4 hrs later after the addition of DTT by dialysis against water using membrane with MWCO of 100 kDa.

Lysozyme Encapsulation.

10 mg of lysozyme was dissolved in 1 mL of milliQ water. 21 μL of $MgCl_2$ solution (100 mM) was added to 379 μL of lysozyme solution. Then, 100 μL of P2 solution was added into lysozyme-$MgCl_2$ solution followed by the addition of 0.1 eq of DTT after 2 hrs. The cross-linking reaction was allowed to undergo for 4 hrs. The unloaded lysozyme was removed by extensively dialysis against water using membrane with MWCO of 100 kDa.

VesiGel functionalization. Cationic VesiGel solution was added to 1 mL of DMSO solution. Then, the solution was adjusted to pH 9 by the addition of $NaHCO_3$ solution. Then 0.2 equivalent of TRITC (to the amine) in DMSO was added to the nanoparticle solution. After 24 hours, 0.2 eq. thiol functionalized fluorescein solution in DMSO was also added to the reaction mixture. The reaction mixture was dialysis against MeOH using membrane with MWCO of 11000 Da.

PEGylation of cationic VesiGel. To 500 uL of 2 mg/mL cationic VesiGel solution (0.0022 mmol repeat unit), 500 μL of DMSO was added with 0.95 μL of triethylamine (0.0066 mmol, 3 eq.). 8.8 mg (0.0044 mmol, 2 eq.) of PEG-NHS ester (Mn: 2000 Da) was dissolved in 500 μL of DMSO and then added to the VesiGel solution. The reaction was allowed to go overnight. The free PEG was removed by dialysis against water.

PEGylation of anionic VesiGel. To 2 mL of 1 mg/mL of anionic VesiGel solution (0.0054 mmol repeat unit), 2.07 mg EDC (0.0108 mmol, 2 eq.) was added. Then, 6 mg (0.0108 mmol, 2 eq.) of PEG-$NH_2$ (Mn: 550 Da) in 500 μL of water solution was added to VesiGel solution. The reaction was kept for 24 hrs. The free PEG was removed by dialysis against water.

In this specification and the appended claims, the singular forms "a," "an," and "the" include plural reference, unless the context clearly dictates otherwise. Unless defined otherwise, all technical and scientific terms used herein have the same meaning as commonly understood too one of ordinary skill in the art. Unless defined otherwise, all technical and scientific terms used herein have the same meaning as commonly understood by one of ordinary skill in the art. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A polymer-based nanoparticle having a vesicular structure stabilized by intraparticular crosslinking inside the vesicular structure, wherein the polymer comprises the monomer unit:

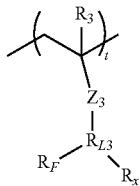

wherein $Z_3$ is

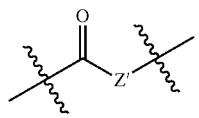

wherein $Z'$ is selected from O or NH;
$R_3$ is selected from H, $C_1$-$C_{12}$ alkyl group, or halogen;
$R_{L3}$ is $CR_4$, wherein $R_4$ is H, $C_1$-$C_{12}$ alkyl group or halogen;
$R_F$ comprises $C(O)(NH)CH_2CH_2NH_2$ or C(O)NH(oligoethylene glycol);
$R_x$ is a crosslinking group capable of inter- or intra-molecular crosslinking or an inter- or intra-molecularly crosslinked group, selected from pyridinyl disulfide and thiol; and
r is an integer from about 10 to about 1000.

2. The polymer-based nanoparticle of claim 1, wherein $R_F$ comprises $C(O)$ $NHCH_2CH_2NH_2$.

3. The polymer-based nanoparticle of claim 2, wherein $R_x$ comprises pyridinyl disulfide.

4. The polymer-based nanoparticle of claim 2, wherein $R_x$ comprises thiol.

5. The polymer-based nanoparticle of claim 1, wherein $R_F$ comprises a C(O)NH (oligoethylene glycol) group.

6. The polymer-based nanoparticle of claim 5, wherein $R_x$ comprises pyridinyl disulfide.

7. The polymer-based nanoparticle of claim 5, wherein $R_x$ comprises thiol.

8. The polymer-based nanoparticle of claim 6, wherein $Z'$ is NH, $R_3$ is H, and $R_{L3}$ is CH.

9. The polymer-based nanoparticle of claim 1, wherein the nanoparticle is surface functionalized by a peptide, a nucleic acid, or a molecular ligand.

10. A nano-assembly comprising:
a host crosslinked polymer-based nanoparticle having a vesicular structure according to claim 1; and
a hydrophilic guest molecular cargo non-covalently encapsulated in the host crosslinked polymer-based nanoparticle,
wherein the host crosslinked polymer is addressable by a biological or chemical intervention resulting in partial or complete decrosslinking of the host polymer and release of the hydrophilic guest molecular cargo from the nano-assembly.

11. The nano-assembly of claim 10, wherein the hydrophilic guest molecular cargo is a therapeutic agent, a diagnostic agent, or an imaging agent.

12. The nano-assembly of claim 10, wherein the hydrophilic guest molecular cargo is a hydrophilic small molecule, a peptide or a nucleic acid.

13. The nano-assembly of claim 12, wherein the hydrophilic guest molecular cargo is a protein or an enzyme.

14. The nano-assembly of claim 11, wherein $Z'$ is NH, $R_3$ is H, $R_{L3}$ is CH, $R_F$ comprises C(O)NH (oligoethylene glycol), and $R_x$ comprises pyridinyl disulfide.

* * * * *